US011963764B2

(12) United States Patent
Khan et al.

(10) Patent No.: US 11,963,764 B2
(45) Date of Patent: Apr. 23, 2024

(54) PRINTED ALL-ORGANIC REFLECTANCE OXIMETER ARRAY

(71) Applicant: The Regents of the University of California, Oakland, CA (US)

(72) Inventors: Yasser Khan, Berkeley, CA (US); Donggeon Han, Berkeley, CA (US); Adrien Pierre, Berkeley, CA (US); Jonathan Ting, Berkeley, CA (US); Xingchun Wang, Berkeley, CA (US); Claire Meyer Lochner, Berkeley, CA (US); Ana Arias, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 379 days.

(21) Appl. No.: 17/101,832

(22) Filed: Nov. 23, 2020

(65) Prior Publication Data
US 2021/0393176 A1    Dec. 23, 2021

Related U.S. Application Data

(63) Continuation of application No. PCT/US2019/033381, filed on May 21, 2019.
(Continued)

(51) Int. Cl.
*A61B 5/1455* (2006.01)
(52) U.S. Cl.
CPC .... *A61B 5/14551* (2013.01); *A61B 2562/046* (2013.01); *A61B 2562/164* (2013.01)
(58) Field of Classification Search
CPC .............. A61B 5/1455; A61B 5/14551; A61B 5/14552; A61B 5/68; A61B 5/6802;
(Continued)

(56) References Cited

U.S. PATENT DOCUMENTS

| 4,167,331 A | 9/1979 | Nielsen |
| 4,807,630 A | 2/1989 | Malinouskas |

(Continued)

FOREIGN PATENT DOCUMENTS

EP    3035244 A1    6/2016

OTHER PUBLICATIONS

Written Opinion of the International Search Authority, dated Jul. 10, 2019, in Application No. PCT/US2019/033381.
(Continued)

*Primary Examiner* — Chu Chuan Liu
(74) *Attorney, Agent, or Firm* — Gerald T. Gray; Leydig, Voit & Mayer, LTD.

(57) ABSTRACT

A flexible oximeter device for measuring pulse and blood oxygen saturation in tissue includes a first array of first light emitting elements that emit red light, a second array of second light emitting elements that emit green light or near-infrared (NIR) light and an array of sensor elements arranged on at least one flexible substrate. Each sensor element is configured to detect red and green or NIR light, and to output a signal representing an amount of red or green or NIR light detected. The first and second arrays and the array of sensor elements form a plurality of interleaved measurement pixels, each pixel comprising one of the first light emitting elements and a corresponding sensor element, and one of the second light emitting elements and a different corresponding sensor element.

24 Claims, 12 Drawing Sheets

Overview and operation of a printed reflectance oximeter array (ROA) according to an embodiment.

Related U.S. Application Data

(60) Provisional application No. 62/674,264, filed on May 21, 2018.

(58) Field of Classification Search
CPC ............ A61B 5/0205; A61B 5/02416; A61B 2562/046; A61B 2562/164; A61B 2562/066; A61B 2562/12
See application file for complete search history.

(56) References Cited

U.S. PATENT DOCUMENTS

| | | | |
|---|---|---|---|
| 5,040,539 A | | 8/1991 | Schmitt et al. |
| 5,791,345 A | | 8/1998 | Ishihara |
| 5,830,137 A | | 11/1998 | Scharf |
| 6,330,468 B1 | | 12/2001 | Scharf |
| 6,801,648 B2* | 10/2004 | Cheng ................ A61B 5/14551 600/431 |
| 10,548,519 B2 | | 2/2020 | Arias et al. |
| 2002/0019587 A1* | 2/2002 | Cheng ................ A61B 5/14551 250/341.1 |
| 2007/0129613 A1 | | 6/2007 | Rochester et al. |
| 2008/0312517 A1* | 12/2008 | Genoe ................ A61B 5/14551 257/E31.115 |
| 2010/0241006 A1* | 9/2010 | Choi .................... A61B 5/0084 600/544 |
| 2011/0112379 A1 | | 5/2011 | Li |
| 2013/0133822 A1 | | 5/2013 | Koetse |
| 2013/0261415 A1 | | 10/2013 | Ashe |
| 2014/0128695 A1* | 5/2014 | Fang .................. A61B 5/14552 600/323 |
| 2016/0302674 A1 | | 10/2016 | Moyer |
| 2017/0360316 A1* | 12/2017 | Gu ........................ A61B 5/7475 |

OTHER PUBLICATIONS

International Search Report of the International Search Authority, dated Jul. 10, 2019, in Application No. PCT/US2019/033381.
Lochner et al., "All-organic optoelectronic sensor for pulse oximetry," Nature Communications, vol. 5, Dec. 10, 2014.
Lochner et al., "Supplementary information: All-organic optoelectronic sensor for pulse oximetry," Nature Communications, vol. 5, pp. 1-5, Dec. 10, 2014.
Chiou et al., "An integrated CMOS optical sensing chip for multiple bio-signal detections," 2016 IEEE Asian Solid-State Circuits Conference (A-SSCC), IEEE, pp. 197-200, Nov. 7, 2016.
Khan et al., "System design for organic pulse oximeter," 2015 6th International Workshop on Advances in Sensors and Interfaces (IWASI), IEEE, pp. 83-86, Jun. 18, 2015.
Yindar Chuo et al. "Platform for All-Polymer-Based Pulse-Oximetry Sensor", IEEE Sensors 2010 Conference, School of Engineering Science, pp. 155-159.
WJ Cui et al., "In Vivo Reflectance of Blood and Tissue as a Function of Light Wavelength", IEEE Trans Biomed Eng., 190, Jun:37(6):632-9.
Rasmus G. Haahr, "An Electronic Patch for Wearable Health Monitoring by Reflectance Pulse Oximetry", IEEE Transactions on Biomedical Circuits and Systems, pp. 1-9.
Sandberg et al. "Non-invasive Monitoring of Muscle Blood Perfusion by Photoplethysmography: Evaluation of a New Application", Acta Physiol Scand, 2005:183, 335-343.
Tamura et al., "Wearable Photoplethysmographic Sensors—Past and Present", Electronics, 2014:3:282-302, ISSN 2079-9292.
International Search Report and Written Opinion dated Oct. 19, 2015, International Application No. PCT/US2015/042107.
Sekitani et al., "Flexible Organic Transistors and Circuits with Extreme Bending Stability," NMAT, vol. 9, pp. 1015-1022, 2010.
International Preliminary Report on Patentability issued in PCT/US2015/042107 dated Jan. 24, 2017.
Mendelson, "Pulse Oximetry," Wiley Encyclopedia of Biomedical Engineering, pp. 1-18, 2006.
U.S. Appl. No. 15/414,397, filed Jan. 24, 2017.

* cited by examiner

*Overview and operation of a printed reflectance oximeter array (ROA) according to an embodiment.*

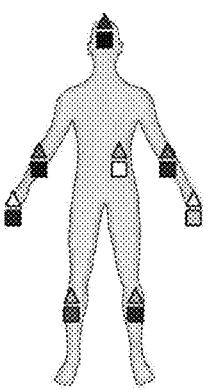
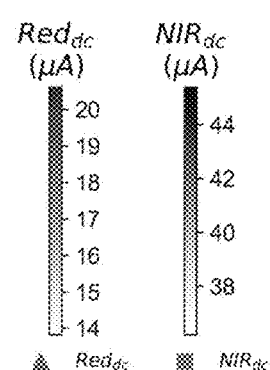
FIG. 2C
FIG. 2D
FIG. 2E
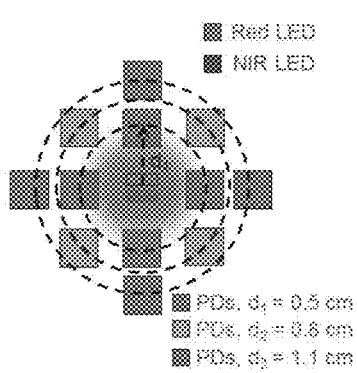
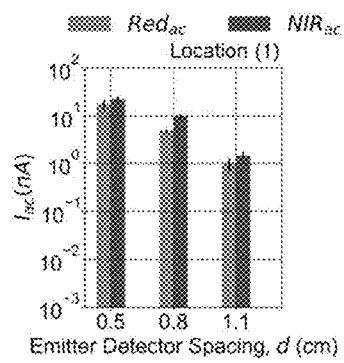
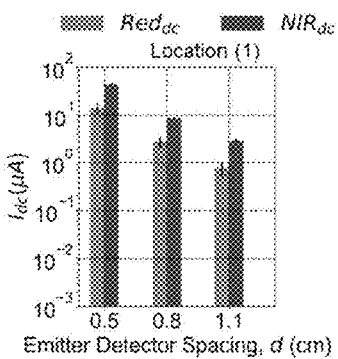
*Sensor placement and emitter-detector spacing (d) for reflectance oximetry.*

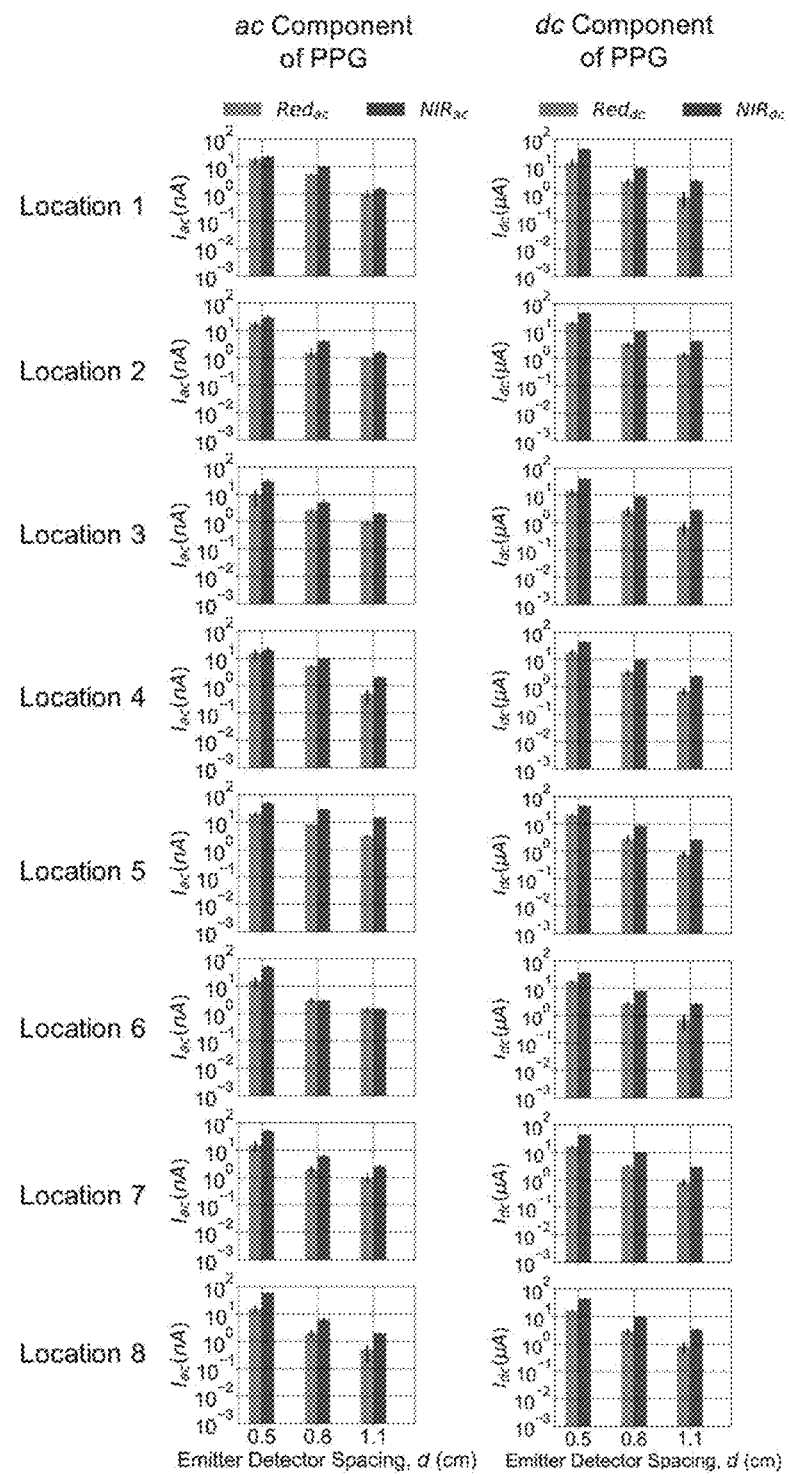
*FIG. 3 Emitter-detector spacing (d) study data*

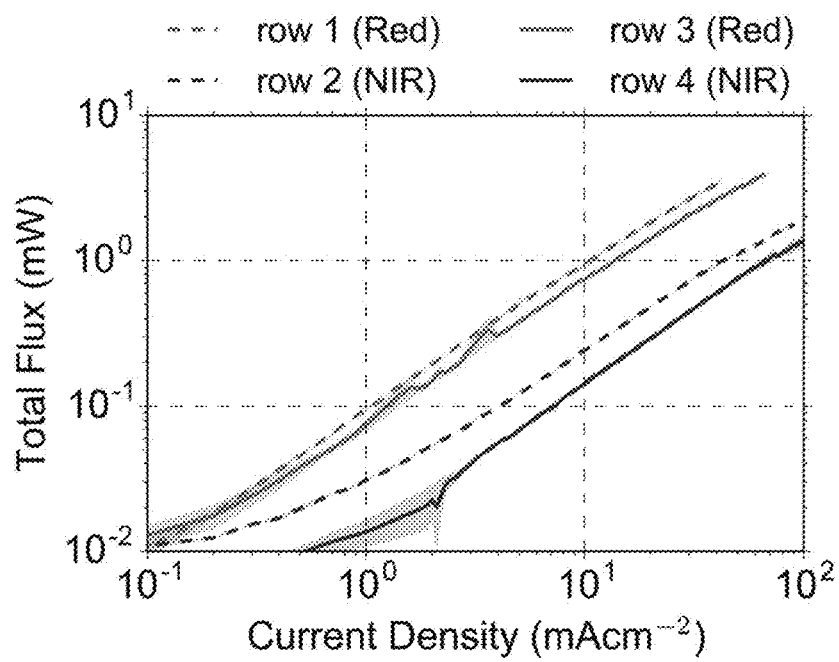
FIG. 4 *Current Density vs. Total Flux for the OLEDs.*
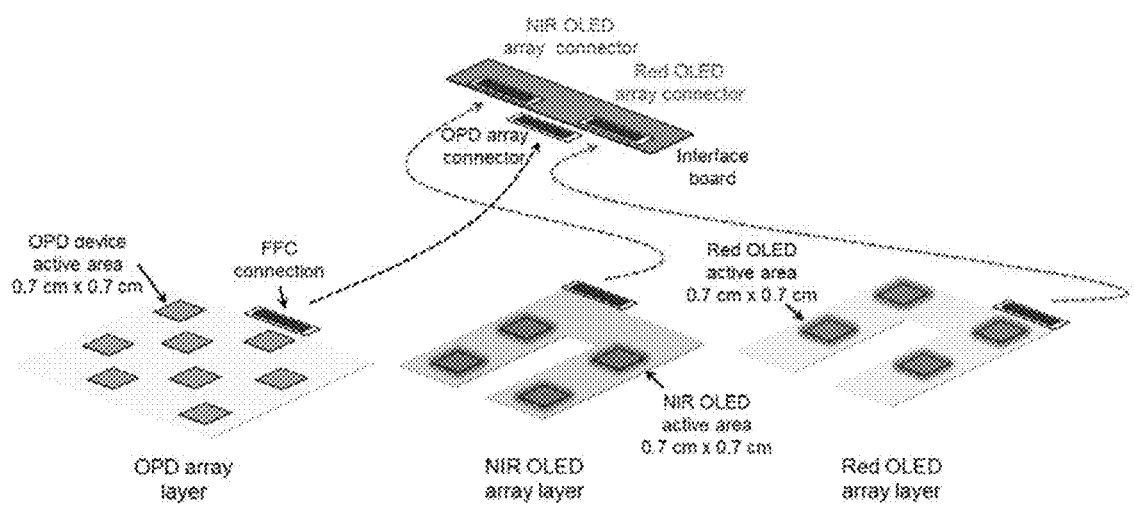
FIG. 5 *Reflectance oximeter array assembly.*

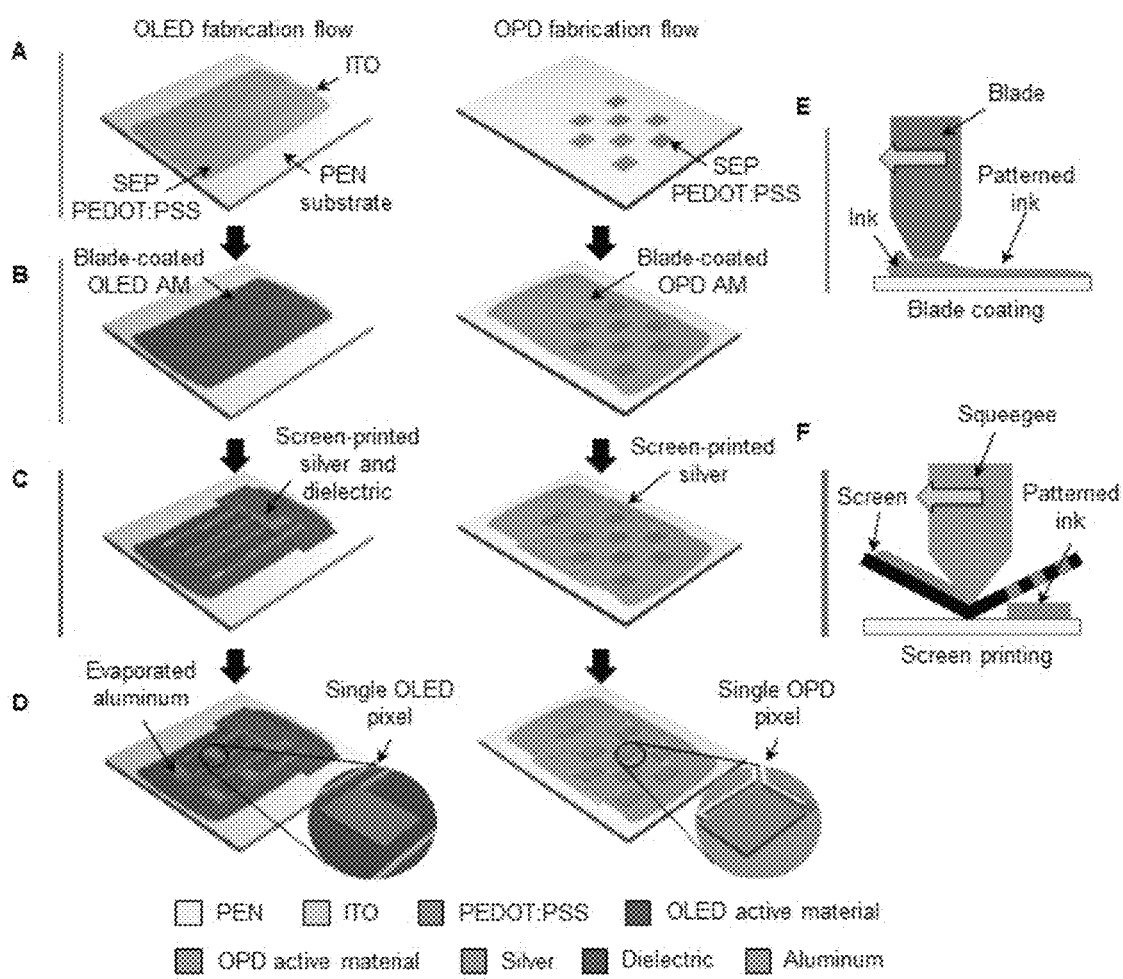
*FIG. 6. Fabrication flow of the OLED and OPD arrays for the ROA.*

Red / NIR OLED structure

OPD structure

Device structure embodiments: (A) OLED; (B) OPD.

*Photographs and performance parameters of OPD and OLED arrays.*

*System design for reflectance oximetry and single pixel reflection-mode pulse oximetry ($SpO_2^r$) results.*

■ Analog switch (Red)   ▨ Analog switch (NIR)
▨ Analog switch (OPD)   ■ Analog front end
■ FFC connector (OPD)

*Control electronics and connections of the oximeter system.*

FIG. 11A Single pixel mode    FIG. 11B Array mode
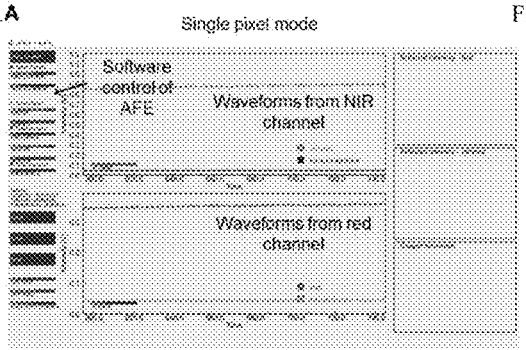
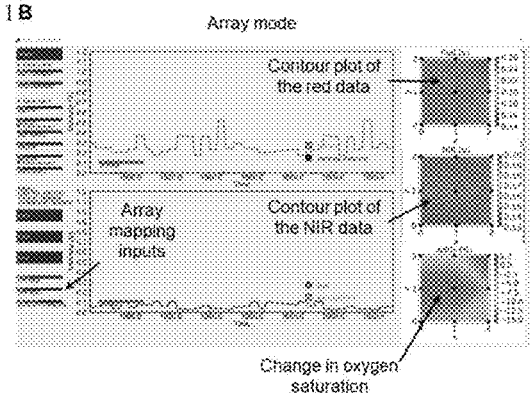
*Graphical User Interface (GUI) for processing and visualizing the oximeter data.* in-vivo 2D oxygen saturation monitoring with the reflectance oximeter array (ROA).

*PPG signal from the red and NIR channels of the ROA before and after pressure cuff-induced ischemia*

PRINTED ALL-ORGANIC REFLECTANCE OXIMETER ARRAY

CROSS REFERENCES

The present application is a continuation of PCT/US2019/033381, entitled "Printed All-Organic Reflectance Oximeter Array," which was filed on May 21, 2019, and which claims priority to U.S. Provisional Patent Application No. 62/674,264 by Khan et al., entitled "Printed All-Organic Reflectance Oximeter Array," filed May 21, 2018. Both applications are incorporated in their entirety herein by reference.

BACKGROUND

The present disclosure provides systems and methods to measure pulse and blood oxygen saturation in living tissue using reflectance spectroscopy.

A blood oximeter measures oxygen saturation percentage in human blood by comparing the amount of light absorbed by the blood (which has different molar extinction coefficients depending on the incident light's wavelength and whether or not the hemoglobin is oxygenated or deoxygenated) at two different wavelengths. Ideally, the molar extinction coefficients of oxygenated and deoxygenated blood will differ substantially at each of the two wavelengths used. Traditionally, red and infrared light is transmitted through human tissue (e.g., ear or finger) and detected to determine oxygen saturation. LEDs are placed on one side of the tissue and a detector placed on the other side. Sampling of the transmitted light provides information about the ratio of oxygenated and deoxygenated hemoglobin in the blood. Such pulse oximeters, however, tend to be bulky and rigid and their use limited to certain tissue areas where sufficient light transmission in the red and IR wavelengths can occur.

BRIEF SUMMARY

The present disclosure provides systems and methods to measure pulse and blood oxygen saturation in tissue using reflectance spectroscopy. The flexible reflectance oximeter array (ROA) embodiments disclosed herein may be used beyond the conventional sensing locations because of the novel sensor configurations. The mechanical flexibility, 2D oxygenation mapping capability, and the ability to place the sensor in various locations make the ROA embodiments promising for novel medical sensing applications such as mapping oxygenation in tissues, wounds, skin grafts, or transplanted organs.

According to an embodiment, an oximeter device (e.g., pulse oximeter device) is provided that includes a first array of first light emitting elements that emit red light, a second array of second light emitting elements, wherein each second light emitting element emits green light or near-infrared (NIR) light, wherein the first array and the second array are arranged on at least one flexible substrate in an interleaved manner, and an array of sensor elements arranged on the at least one flexible substrate, wherein each sensor element is configured to detect red and green light or red and NIR light, and to output a signal representing an amount of red or green or NIR light detected, wherein the first array and the second array and the array of sensor elements form a plurality of interleaved measurement pixels, each measurement pixel comprising one of said first light emitting elements and a corresponding sensor element adjacent thereto, and one of said second light emitting elements and a different corresponding sensor element adjacent thereto.

According to an embodiment, an oximeter device is provided that typically includes a first array of first light emitting elements that emit red light, a second array of second light emitting elements, wherein each second light emitting element emits green light or near-infrared (NIR) light, wherein the first array and the second array are arranged on a first flexible substrate in an interleaved manner, and an array of sensor elements arranged on a second flexible substrate, wherein each sensor element is configured to detect red and green light or red and NIR light, and to output a signal representing an amount of red or green or NIR light detected, wherein the first substrate and the second substrate are coupled together to form a plurality of interleaved measurement pixels, each measurement pixel comprising one of said first light emitting elements and a corresponding sensor element adjacent thereto, and one of said second light emitting elements and a different corresponding sensor element adjacent thereto.

In certain aspects, each of said first light emitting elements and each of said second light emitting elements comprises an organic light emitting diode (OLED), and wherein each of said sensor elements comprises an organic photodiode (OPD). In certain aspects, the oximeter device further includes control electronics electronically coupled with the first light emitting elements, the second light emitting elements, and the sensor elements and configured to control activation of the first and second light emitting elements and receive the signals output by the sensor elements. In certain aspects, the control electronics includes a signal processor that receives and processes the signals output by the sensor elements to produce signals that represent blood oxygenation content. In certain aspects, the at least one flexible substrate comprises polyethylene naphthalate (PEN). In certain aspects, each of said sensor elements is configured to detect the emitted red or green or NIR light reflected by tissue containing blood. In certain aspects, the first array and the second array and the array of sensor elements are arranged on a single flexible substrate in the interleaved manner forming the plurality of interleaved measurement pixels. In certain aspects, the first array and the second array are arranged on a first flexible substrate in the interleaved manner, wherein the array of sensor elements are arranged on a second flexible substrate, and wherein the first flexible substrate and the second flexible substrate are coupled together to form the plurality of interleaved measurement pixels. In certain aspects, the first array is arranged on a first flexible substrate and the second array is arranged on a second flexible substrate, wherein the array of sensor elements are arranged on a third flexible substrate, and wherein the first flexible substrate, the second flexible substrate and the third flexible substrate are coupled together to form the plurality of interleaved measurement pixels.

According to yet another embodiment, a flexible oximeter device is provided that typically includes a first N×M array of first light emitting elements that emit red light, a second N×M array of second light emitting elements, wherein each second light emitting element emits green light or near-infrared (NIR), and a third array of 2*N*M sensing elements, each sensing element being configured to detect red and green light or red and NIR light and to output a signal representing an amount of red or green or NIR light detected, wherein N and M are each equal to or greater than 1, wherein the first array, the second array and the third array are arranged on at least one flexible substrate in an interleaved manner forming a (2N−1)×(2M−1) array of interleaved measurement pixels, each said measurement pixel comprising one of said first light emitting elements and a corresponding sensing element, and one of said second light emitting elements and a different corresponding sensing element.

In certain aspects, N=M, and wherein N is greater than or equal to 2. In certain aspects, a first spacing between each sensing element and each first light emitting element and a second spacing between each sensing element each second light emitting element are substantially the same. In certain aspects, the first and second spacings are each between about 0.1 cm and about 1.2 cm, e.g., between about 0.5 cm and about 1.0 cm. In certain aspects, the pitch of the optoelectronic devices, e.g., light emitter and detector spacing, is between about 0.1 cm and 1.2 cm; the desired pitch depends on the optical flux output of the light emitters, external quantum efficiency (EQE) of the light detectors, the active area of the light emitters and the size and/or composition of the light detectors. In certain aspects, each of said first light emitting elements and each of said second light emitting elements comprises an organic light emitting diode (OLED), and wherein each of said sensing elements comprises an organic photodiode (OPD). In certain aspects, the at least one flexible substrate comprises polyethylene naphthalate (PEN). In certain aspects, the first N×M array and the second N×M array are arranged on a first flexible substrate, and wherein the third array of sensing elements is arranged on a second flexible substrate that is attached to the first flexible substrate. In certain aspects, each said sensing element is configured to detect emitted red or green or NIR light reflected by tissue containing blood.

According to yet a further embodiment, a method of spatially mapping oxygenation content in a tissue sample is provided. The method typically includes placing an oximeter device having an array of interleaved measurement pixels proximal to an area of a tissue sample, each said measurement pixel corresponding to a different measurement location of the area of the tissue sample, taking measurements of the tissue sample using each measurement pixel in an order, and creating a map of oxygenation content of the area of the tissue sample based on the measurements taken of the tissue sample. In certain aspects, taking measurements includes, for each said measurement pixel, activating the first light emitting element, detecting a reflected red light signal using the first corresponding sensing element, activating the second light emitting element, and detecting a reflected green or NIR light signal using the second corresponding sensing element. In certain aspects, the order of taking measurements is a sequential order. In certain aspects, the area of the tissue sample exhibits a pulsatile arterial blood signal. In certain aspects, the area of the tissue sample does not exhibit a pulsatile arterial blood signal. In certain aspects, the method further includes displaying a representation of the map of oxygenation content of the area of the tissue sample on a display device.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

The detailed description is described with reference to the accompanying figures. The use of the same reference numbers in different instances in the description and the figures may indicate similar or identical items.

FIG. 1A shows a flexible optoelectronic sensor array used to map 2D oxygenation of a skin graft, according to an embodiment.

FIG. 1B shows an ROA comprising 4 red and 4 NIR OLEDS and 8 OPDs according to an embodiment.

FIG. 2C shows a schematic of a setup for the emitter-detector spacing study—rings of four PDs spaced 0.5, 0.8, and 1.1 cm away from the LEDs at the center are used to obtain the signal.

FIG. 2D shows ac signal magnitudes recorded using the sensor board on the wrist for d=0.5, 0.8, and 1.1 cm; data is collected from 5 subjects in 3 separate runs, error bars show the standard deviation of the data.

FIG. 2E shows dc signal magnitudes recorded using the sensor board on the wrist for d=0.5, 0.8, and 1.1 cm; data is collected from 5 subjects in 3 separate runs, error bars show the standard deviation of the data.

FIG. 3 shows emitter-detector spacing (d) study data.

FIG. 4 shows current density vs. total flux for the OLEDs; total flux for OLEDs is shown according to the row position. At the operating condition of 10 $mAcm^{-2}$, the red OLEDs provide 0.9 mW of flux, while the NIR OLEDs provide 0.2 mW of flux.

FIG. 5 shows a reflectance oximeter array assembly according to an embodiment.

FIG. 6. shows a fabrication flow for making OLED and OPD arrays for an ROA according to an embodiment.

Figure 7A:
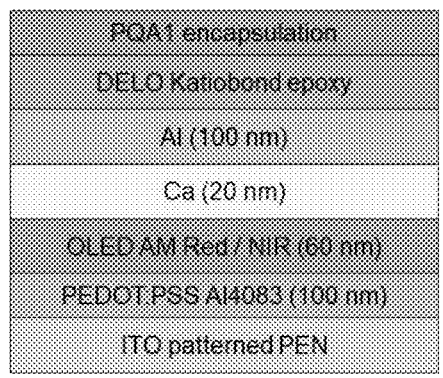

FIG. 7A shows a device structure of an OLED device according to an embodiment.

Figure 7B:
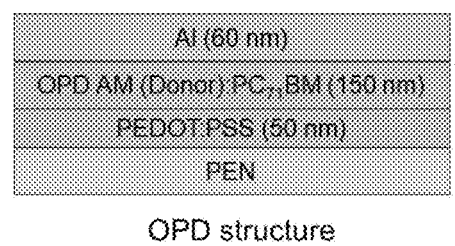

FIG. 7B shows a device structure of an OPD device according to an embodiment.

Figure 8A:
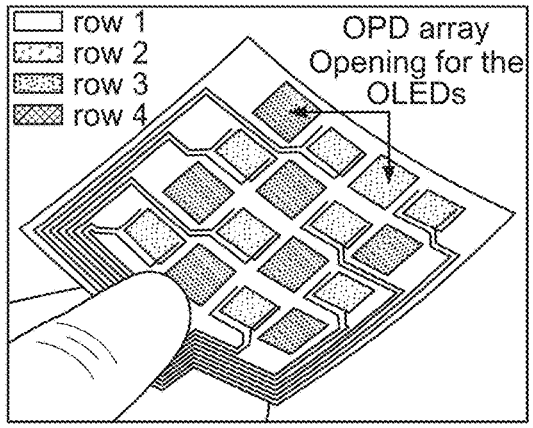

FIG. 8A shows an OPD array composed of 8 pixels—2 pixels in each row—according to an embodiment. The rows are marked using different markers, which represents the legends of performance data presented in the FIGS. 8C-D.

Figure 8B:
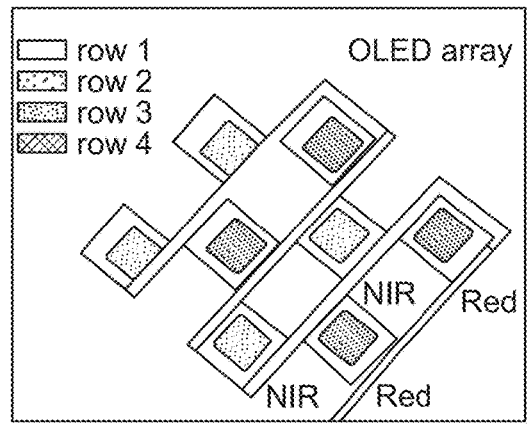

FIG. 8B shows red and NIR OLED arrays—2×2 red OLED array in row 1 and 3, and 2×2 NIR OLED array in row 2 and 4, according to an embodiment. The rows are marked markers, which represents the legends of performance data presented in the FIG. 8F-G.

Figure 8C:
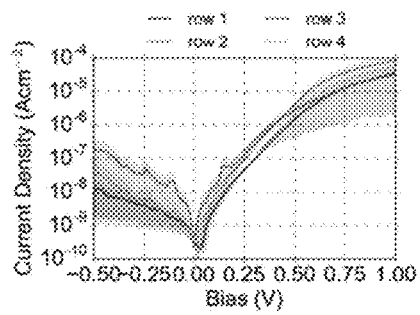

FIG. 8C shows current density vs voltage bias (JV) plot for the OPD array. Here each trace represents mean of the data in that row, while the shaded region shows the range of the data.

Figure 8D:
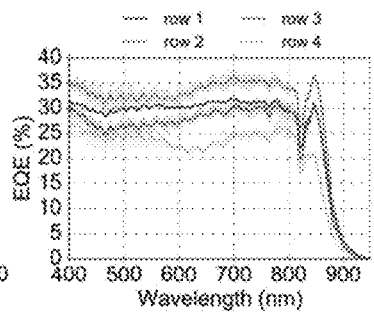

FIG. 8D shows EQE of the OPD pixels in the array as denoted by row position in accordance with FIG. 8A.

Figure 8E:
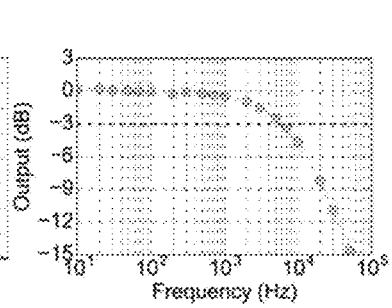

FIG. 8E shows the frequency response of an OPD pixel. The 3 dB cutoff is at over 5 kHz.

Figure 8F:
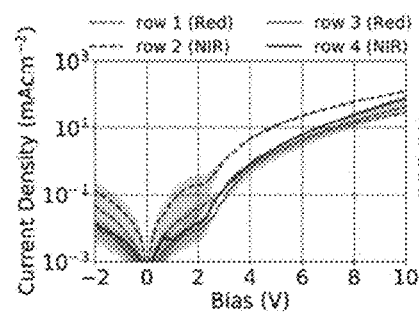

FIG. 8F shows JV characteristics of the red and NIR OLED arrays as denoted by row position in accordance with FIG. 8B.

Figure 8G:
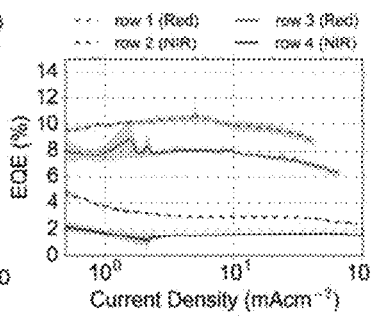

FIG. 8G shows EQE as a function of current density of OLED arrays.

Figure 8H:
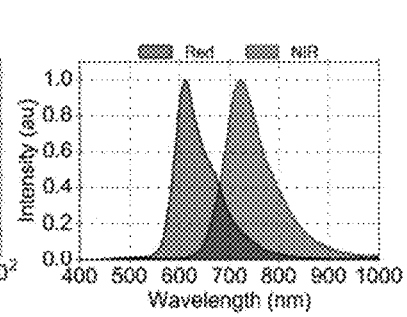

FIG. 8H shows emission spectra of the red and NIR OLED arrays.

Figure 9A:
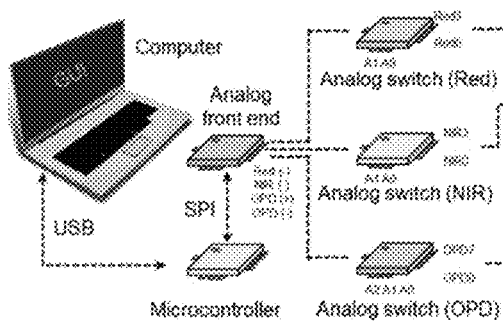

FIG. 9A shows a reflectance oximeter system design according to an embodiment, where each pixel of the ROA (one red and one NIR OLED, and two OPDs) is connected to an analog front end (AFE) using analog switches, for both single pixel and array operation using the control electronics. The AFE drives the OLEDs and reads out the OPD signal. The AFE is controlled using a microcontroller, e.g., an Arduino Due microcontroller, and the data is collected using a Universal Serial Bus (USB) interface, and processed using software.

Figure 9B:
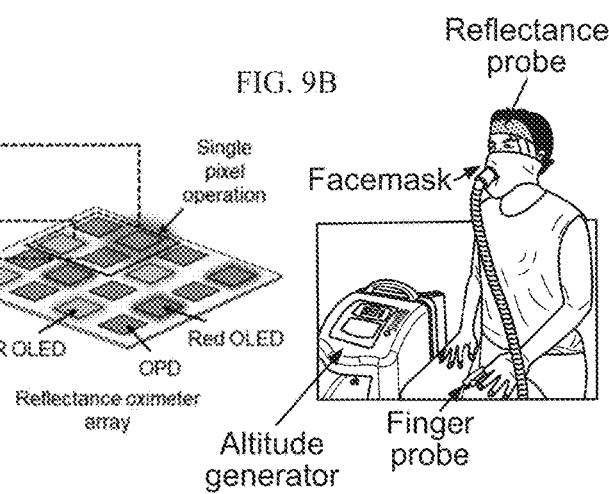

FIG. 9B shows a setup for changing oxygen saturation of human volunteers—an altitude simulator varies the oxygen content of the air the volunteer breathes in via a facemask; the $SpO_2$ is recorded using a commercial probe on the finger and the reflectance oximeter on the forehead.

Figure 9C:
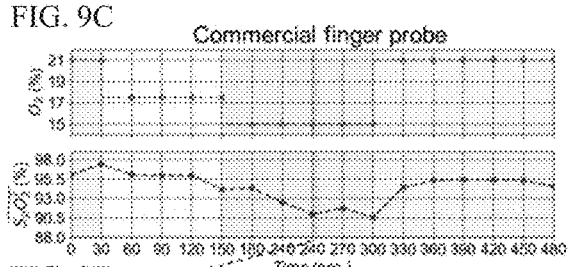

FIG. 9C shows results from the commercial transmission-mode finger probe oximeter ($SpO_2^t$), where the oxygen concentration is changed from 21% to 15%. The oxygen concentration of the air (top panel, blue trace) and calculated oxygen saturation using $SpO_2^t$ (bottom panel, purple trace).

Figure 9D:
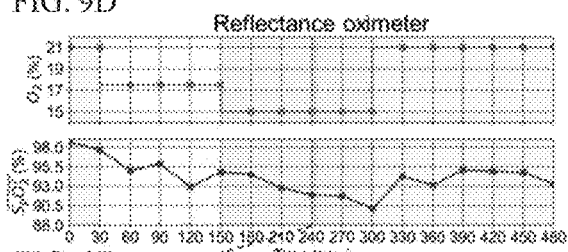

FIG. 9D shows results from the reflectance oximeter ($SpO_2^r$), where the oxygen concentration is changed from 21% to 15%. The oxygen concentration of the air (top panel, blue trace) and calculated oxygen saturation using $SpO_2^r$ (bottom panel, purple trace).

Figure 9E:
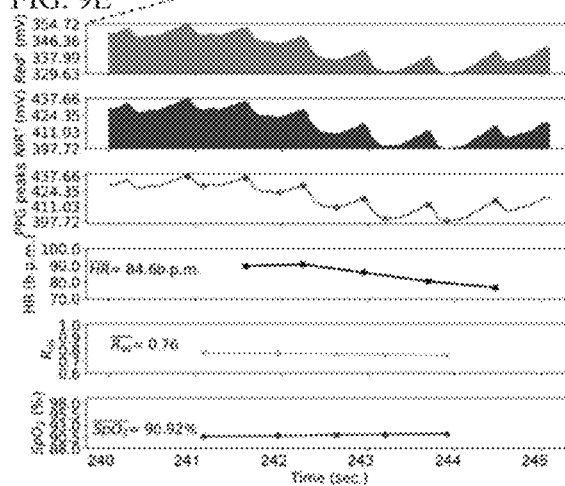

FIG. 9E shows zoomed-in data for the $SpO_2^t$ in FIG. 9C during 240 s<t<245 s show the red channel, NIR channel, PPG peaks, heart rate, $R_{os}$, and $SpO_2$.

Figure 9F:
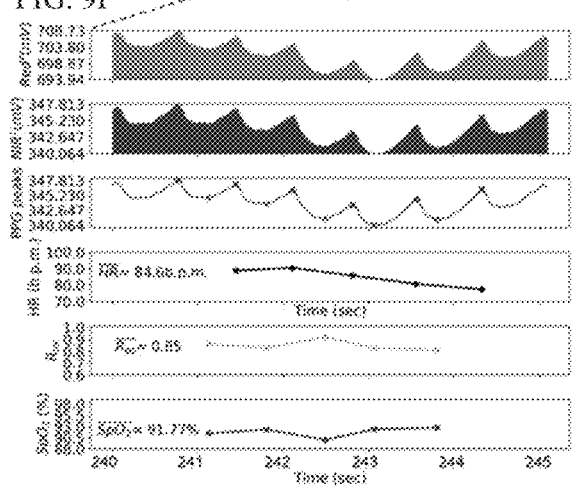

FIG. 9F shows zoomed-in data for the $SpO_2^r$ in FIG. 9D during 240 s<t<245 s show the red channel, NIR channel, PPG peaks, heart rate, $R_{os}$, and $SpO_2$.

Figure 10A:
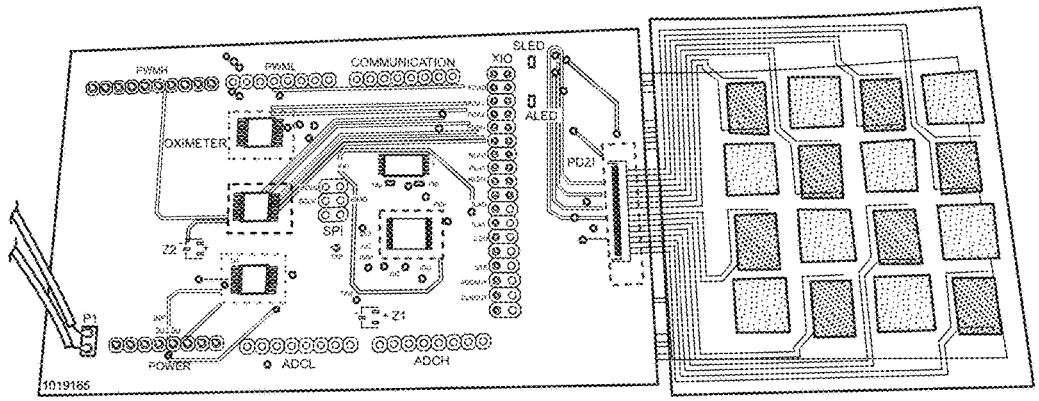

FIG. 10A shows an example of control electronics and connections of the oximeter system; the red and NIR OLED arrays and the OPD array are connected to the control electronics using FFC connectors, and these connections then go through three analog switches to the analog front end (AFE 4490). The AFE connects to the Arduino Due microcontroller over Serial Peripheral Interface (SPI) bus, which provides software control of the ROA.

Figure 10B:
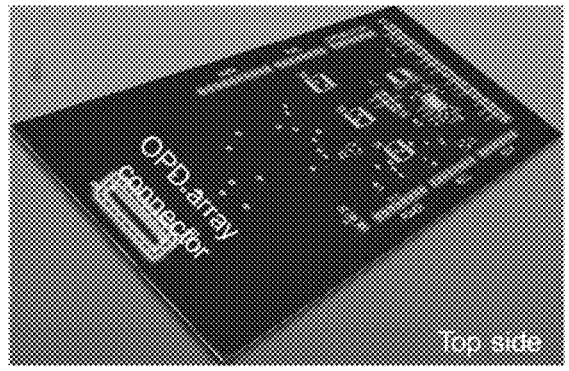

FIG. 10B shows the top side of the controller board, which shows the OPD array connector.

Figure 10C:
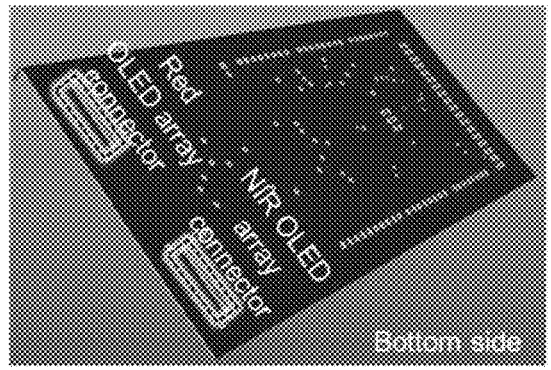

FIG. 10C shows the bottom side of the controller board, which shows the red and NIR OLED array connectors.

FIG. 11A shows a graphical user interface (GUI) for processing and visualizing the oximeter data according to an embodiment; in the single pixel mode, data is collected from a single red and NIR channel, and the waveforms and the background signals are plotted in real-time; the GUI allows software control to tune the OLED drive current and the OPD gain circuitry.

FIG. 11B shows a GUI in an array mode, with data collected from the complete array; contour maps of the red and NIR channels are plotted, in addition to the 2D map of change in oxygen saturation, $\Delta SO_2$.

Figure 12A:
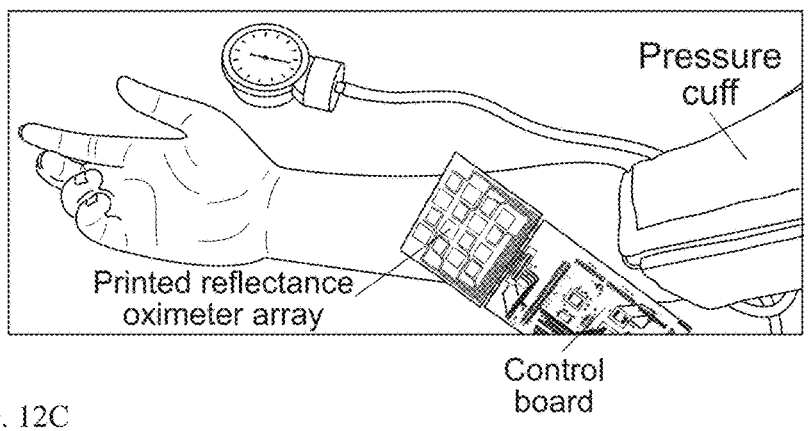

FIG. 12A shows an ROA placed on a volunteer's forearm to monitor the change in oxygen saturation ($\Delta SO_2$). Blood supply to the forearm is controlled by a pressure cuff. The 4×4 devices of the ROA provide 3×3 oximeter pixels.

Figure 12B:
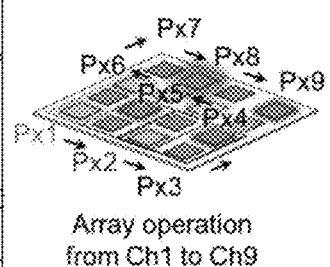

FIG. 12B shows oximeter pixel switching during the array operation; each pixel is composed of one red and one NIR OLED, and two OPDs. A raster scan from Pixel1 (Px1) to Pixel9 (Px9) is used to collect data from the tissue.

Figure 12C:
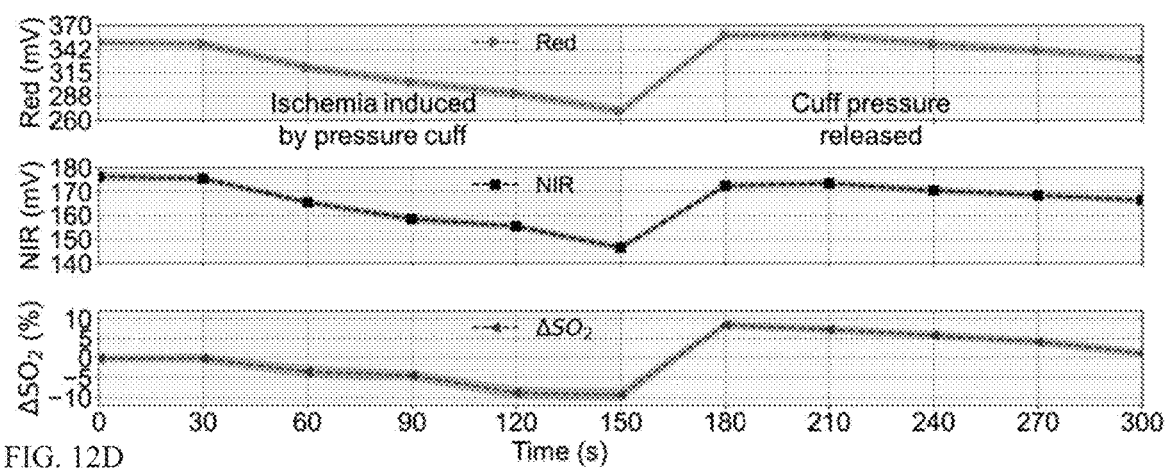

FIG. 12C shows $\Delta SO_2$ for pressure-cuff induced ischemia for a recording of 300 s. Red, NIR, and $\Delta SO_2$ data are shown using red (top), black (middle), and purple (bottom) dotted lines (dotted lines represent the means of the 9 oximeter pixels, shaded region represent the range of the data). Using the pressure cuff, blood supply to the forearm is occluded and restored. In the first 30 s, a baseline reading with no ischemia is taken. The pressure cuff is then inflated to 50 mmHg over the systolic pressure at 30 s<t<150 s, and released at t=150 s. $\Delta SO_2$ varies from 0% under normal condition to −9.3% (t=150 s) under ischemia, and to +8.4% (t=180 s) right after releasing the pressure cuff.

Figure 12D:
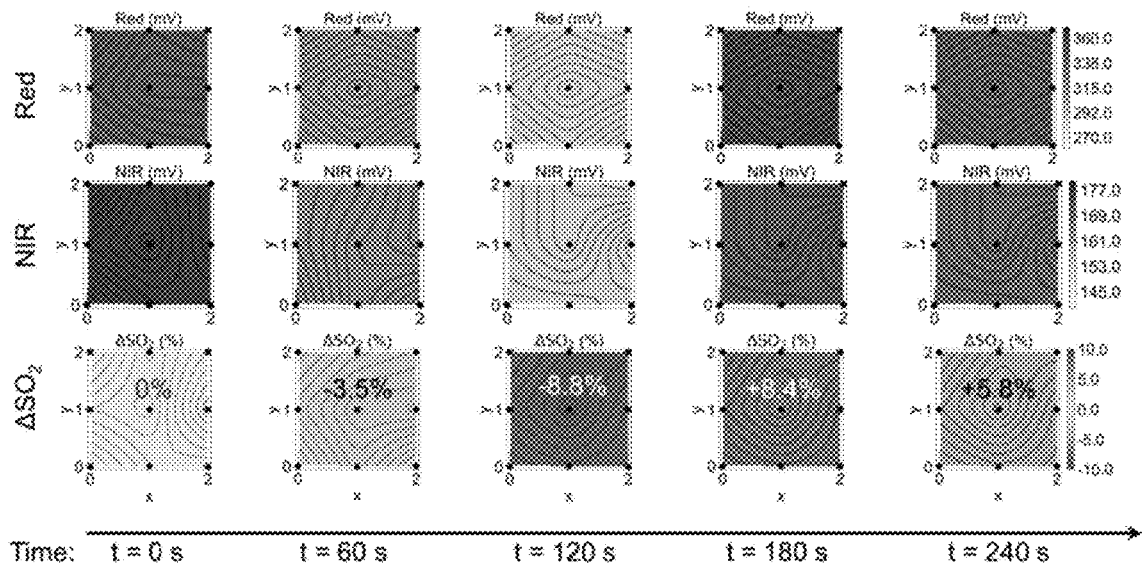

FIG. 12D shows 2D contour maps of red, NIR, and $\Delta SO_2$ under normal condition (t=0 s), under ischemia (t=60,120 s), and after releasing the pressure cuff (t=180,240 s).

Figure 13A:
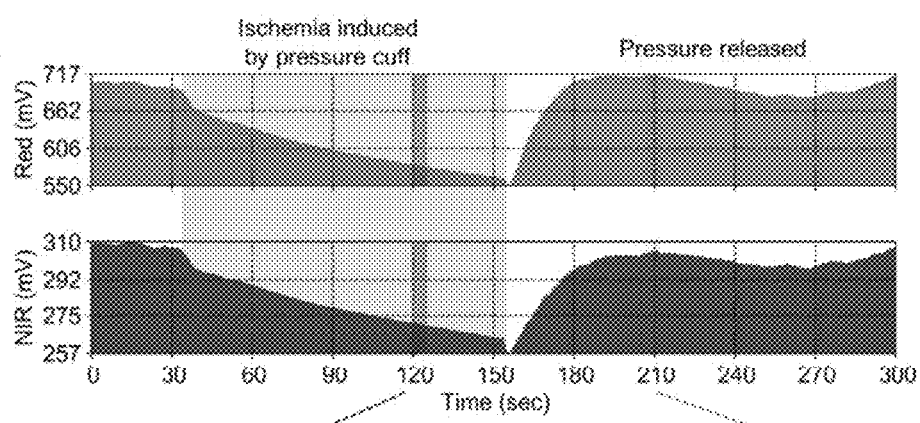

FIG. 13A shows Red and NIR channels of the ROA signal, before and after inducing the ischemia.

Figure 13B:
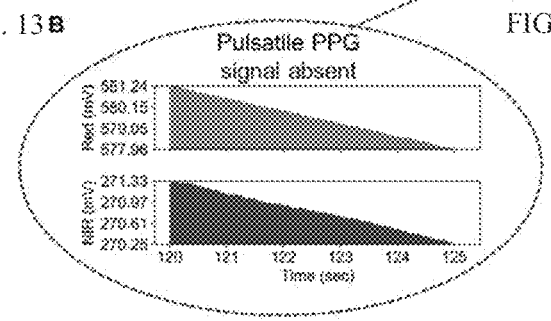

FIG. 13B shows a zoomed-in view of the signal during the pressure cuff-induced ischemia. The pulsatile PPG signal is absent because the blood flood is occluded. Here, reflection-mode pulse oximetry cannot be performed.

Figure 13C:
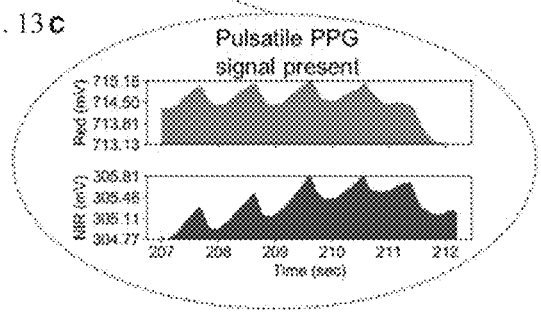

FIG. 13C shows a zoomed-in view of the signal after releasing the pressure. Now, the pulsatile PPG signal is present because the blood flow is restored. In this case, reflection-mode pulse oximetry can be performed.

DETAILED DESCRIPTION

The present disclosure provides systems and methods to measure pulse and blood oxygen saturation in tissue using reflectance spectroscopy. In certain embodiments, the systems and methods use solution processed Light Emitting Diodes (LEDs), such as organic light emitting diodes (OLEDs) and solution processed photodetectors, such as organic polymer photodiodes (OPDs). Two different wavelengths of light (e.g., red and green, or red and infrared) illuminate, or are input onto, an area of human tissue by the OLEDs, and reflected light is recorded by the organic photodetector. The light emitting elements and the sensor or detector element(s) can be positioned on opposite sides of the tissue and traditional transmission measurements made, albeit with red and green light, or the light emitting elements and the detector element(s) can be positioned on the same side of the tissue where the reflection measurements are made.

Hemoglobin, a protein molecule in the blood, transports oxygen from the lungs to the body's tissues. By optically quantifying the concentration of oxyhemoglobin ($HbO_2$) and deoxyhemoglobin (Hb), oxygen saturation ($SO_2$) in tissue can be recorded—this technique is known as oximetry. Pulse oximetry, the most ubiquitous non-invasive method of oximetry, performs this ratiometric optical measurement on pulsatile arterial blood via photoplethysmograph (PPG) at two different wavelengths. Pulse oximeters use optoelectronic sensors composed of light-emitting diodes (LEDs) and photodiodes (PDs) and operate at two distinct wavelengths, conventionally, at red and near-infrared (NIR) wavelengths, where the molar absorptivity of $HbO_2$ and Hb are significantly different (see, e.g., FIG. 1D). While both transmitted and reflected light can be used for pulse oximetry, in transmission-mode pulse oximetry ($S_pO_2^t$), the LEDs shine through the tissue and the transmitted light is collected using the PD on the opposite side—this restricts the sensing locations only to tissues that can be transilluminated, such as the earlobes and the fingers, and the feet for neonates. On the other hand, reflection-mode pulse oximetry ($S_pO_2^r$) uses LEDs and PDs on the same side of the tissue, which allows for diverse sensing locations, such as the forehead, forearm, abdomen, and leg. Additionally, $S_pO_2^r$ provides two-dimensional (2D) oxygenation mapping capability with an array of sensors, whereas only single point measurements can be performed with $S_pO_2^t$.

Existing techniques for measuring oxygen concentration in blood heavily rely on non-invasive transmission-mode pulse oximetry ($SpO_2^t$, which present two fundamental limitations: (1) Sensing locations are limited to only tissues that can be transilluminated; and (2) Only single point measurements can be performed with $SpO_2^t$ due to the sensor configuration. Here, embodiments include a novel flexible and printed electronic system realized by printing and integrating arrays of organic optoelectronics for measuring oxygen saturation in the reflection mode. Two different modes of oximeter operations are disclosed—(i) Reflection-mode pulse oximetry ($SpO_2^r$), when pulsatile PPG signal is present, and (ii) Reflectance oximetry, when pulsatile PPG signal is absent.

Figure 1A:
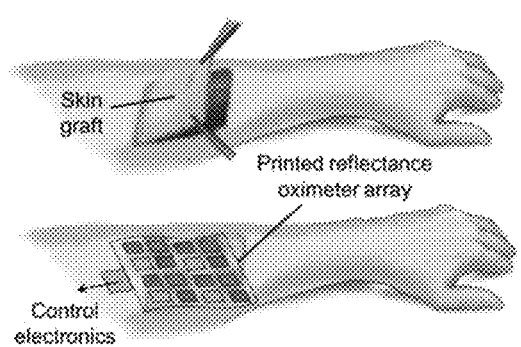
FIG. 1C shows a photograph of the ROA by a patient's forearm.
FIG. 1D shows the molar extinction coefficients of $HbO_2$ and Hb and the ratio of the molar extinction coefficients of Hb and $HbO_2$.

According to embodiments, a reflectance oximeter array (ROA) includes a flexible and printed electronic system realized by printing and integrating arrays of organic optoelectronics to conventional silicon integrated circuits for blood and tissue oximetry. The ROA may be composed of printed red and NIR organic light-emitting diodes (OLEDs), or red and green OLEDs, and organic photodiodes (OPDs). In a specific embodiment, 4 red (612 nm) and 4 NIR (725 nm) OLEDs and 8 OPDs with high sensitivity at the two mentioned wavelengths are used to assemble an ROA as shown in FIG. 1B according to an embodiment. As shown in FIG. 1B, red and NIR OLED arrays composed of 2×2 pixels each are placed side by side, where the pixels are arranged in a checkerboard pattern. The OPD array composed of 8 pixels is placed on top of the OLED arrays. The OLEDs are used as light emitters—$I_0(\lambda)$ is the incident light intensity. OPDs are used to collect the diffused reflected light, $I(\lambda)$. The OLEDs and OPDs are spaced at d cm (emitter-detector spacing). $\mu_a(\lambda)$ is the absorption coefficient of the sensed tissue, which depends on the specific absorption coefficients and concentration of $HbO_2$ and Hb, and DPF is the differential path length factor.

Figure 1C:
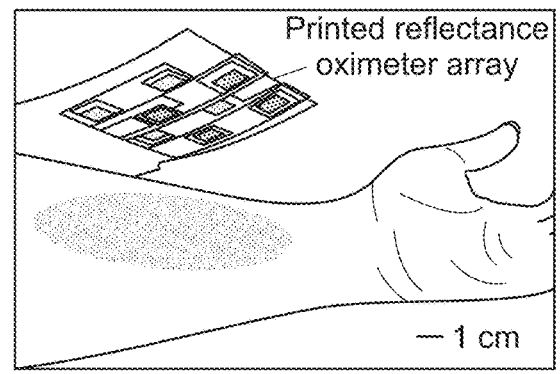
Figure 1B:
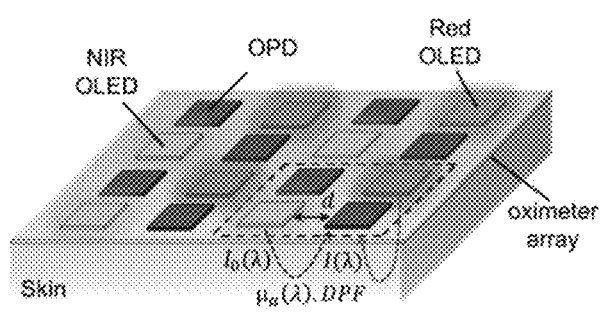

A photograph of the ROA by a patient's forearm is shown in FIG. 1C. In certain aspects, organic optoelectronics and printing techniques are utilized to fabricate the sensor on flexible plastic substrates, resulting in a sensor array that is comfortable to wear and having an increased SNR by establishing a high-fidelity sensor-skin interface. The reflectance oximeter was used to measure $S_pO_2^r$ on the forehead with 1.1% mean error compared to commercial transmission-mode pulse oximeters. In the case of a medical shock, low blood perfusion, or organ injury, the pulsatile arterial blood signal of photoplethysmography (PPG) becomes too weak to be used for pulse. For the aforementioned cases and locations on the body with a low PPG signal, a method is provided to determine $SO_2$ in the absence of pulsatile blood signal. Also, the array embodiments of the ROA allows for creation of a 2D mapping of $SO_2$ of an area rather than a single point. By utilizing the array, oxygenation values of a patient's tissue may be mapped.

The non-invasive 2D oxygenation mapping capability has the potential to transform medical sensing by enabling oxygenation monitoring of tissues and organs during and after surgery. One such application scenario, where a flexible optoelectronic sensor array is used to map 2D oxygenation of a skin graft is illustrated in FIG. 1A. This in-vivo spatial oxygenation mapping device can aid in assessing tissue damage and injury susceptibility Flexible organic and inorganic optoelectronics enhance the SNR of oximetry by reducing the ambient noise signal. The ROA embodiments herein increase the sensing locations of oximetry and enable measuring oxygenation in the absence of pulsatile arterial blood signal. Additionally, the use of printing techniques such as blade coating and screen printing to fabricate the sensor on flexible plastic substrates makes the sensor both comfortable to wear and efficient at extracting high-quality biosignal.

Figure 1D:
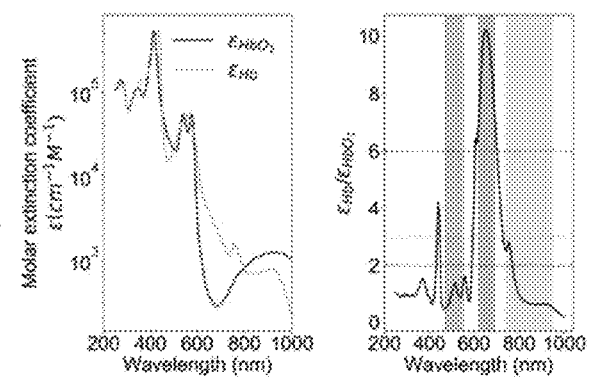

Oximeters utilize the property that the molar extinction coefficients of Hb and $HbO_2$ vary appreciably over the visible and near-infrared (NIR) spectrum (FIG. 1D). If two regions in the spectrum are chosen so that in one region, Hb has a higher absorptivity than $HbO_2$, and in the other region, Hb has a lower absorptivity than $HbO_2$, a ratiometric measurement can be performed to obtain the concentration of $HbO_2$ and Hb. The oxygen saturation ($SO_2$) is the concentration of $HbO_2$ divided by the sum of the concentration of $HbO_2$ ($C_{HbO_2}$) and Hb ($C_{Hb}$):

$$SO_2 = \frac{C_{HbO_2}}{C_{HbO_2} + C_{Hb}} \quad (1)$$

In FIG. 1D, three regions are shown: (1) green ($\varepsilon_{Hb}/\varepsilon_{HbO_2}$<2), (2) red ($\varepsilon_{Hb}/\varepsilon_{HbO_2}$>6), and (3) NIR ($\varepsilon_{Hb}/\varepsilon_{HbO_2}$<3). Therefore, the combinations of "red and green" or "red and NIR" can be used for oximetry because of the contrast in molar extinction coefficients. As discussed earlier, the operation of noninvasive reflectance oximetry can be grouped into two modes: (i) Reflection-mode pulse oximetry ($SpO_2^r$), when pulsatile PPG signal is present, and (ii) Reflectance oximetry, when pulsatile PPG signal is absent.

Reflection-Mode Pulse Oximetry ($SpO_2^r$)

In the case of $SpO_2^r$, a modified Beer-Lambert's law can be used to model the light propagation in tissue as shown in FIG. 1B and the equation below:

$$I(\lambda) = I_0(\lambda) e^{-\mu_a(\lambda) \cdot d \cdot DPF(\lambda)} \quad (2)$$

Where $I(\lambda)$ is the measured diffused reflected light intensity, $I_0(\lambda)$ is the incident light intensity, $\mu_a(\lambda)$ is the absorption coefficient of the sensed tissue, d is the distance between the light emitter and detector, and $DPF(\lambda)$ is the differential pathlength factor (DPF), which accounts for the multiple scattering of light in tissue.

Pulse oximeters measure light attenuation in pulsatile arterial blood using "red and green" or "red and NIR" wavelengths to calculate $SpO_2$ in accordance with the Beer-Lambert's law and an empirical correction according to the Eq. (3). The complete derivation is provided in the Supplementary Methods section below.

$$S_pO_2^r(R'_{os}) = \frac{\varepsilon_{\lambda_1, Hb} - \varepsilon_{\lambda_2, Hb} R'_{os}}{(\varepsilon_{\lambda_1, Hb} - \varepsilon_{\lambda_1, HbO_2}) + (\varepsilon_{\lambda_2, HbO_2} - \varepsilon_{\lambda_2, Hb}) R'_{os}} \quad (3)$$

Here, $\varepsilon_{\lambda, HbO_2}$ and $\varepsilon_{\lambda, Hb}$ are the molar extinction coefficient of oxyhemoglobin and deoxyhemoglobin at each wavelength.

$$R'_{os} = \frac{R_{os}}{\frac{DPF_{\lambda_1}}{DPF_{\lambda_2}}}, \text{ where } R_{os} = \frac{AC_{\lambda_1}/DC_{\lambda_1}}{AC_{\lambda_2}/DC_{\lambda_2}},$$

is the ratio of pulsatile (ac) to stationary (dc) signals at the two wavelengths, and $DPF(\lambda)$ accounts for the multiple scattering in the reflection mode.

Reflectance Oximetry

A PPG signal from pulsatile arterial blood is essential for pulse oximetry. Therefore, in the case of low perfusion or in the absence of pulsatile arterial blood signal, pulse oximetry in both transmission and reflection mode cannot be performed. In these scenarios, Eq. (2) can be rewritten to measure the time-varying light intensity attenuation, $\Delta I(\lambda)$ in blood and tissue. Here, $\Delta\mu_a$ expresses the change in absorption during the measurement.

$$\Delta I(\lambda) = I_0(\lambda) e^{-\mu_a(\lambda) \cdot d \cdot DPF(\lambda)} \quad (4)$$

$\Delta\mu_a(\lambda)$ can be represented as the sum of the molar extinction coefficients multiplied by the concentrations of $HbO_2$ and $Hb$:

$$\Delta\mu_a(\lambda) = \varepsilon_{HbO_2}(\lambda) \cdot \Delta C_{HbO_2} + \varepsilon_{Hb}(\lambda) \cdot \Delta C_{Hb} \quad (5)$$

Since there are two wavelength channels, a system of linear equations can be established using Eq. (4) and (5):

$$\begin{bmatrix} \varepsilon_{HbO_2}(\lambda_1) & \varepsilon_{Hb}(\lambda_1) \\ \varepsilon_{HbO_2}(\lambda_2) & \varepsilon_{Hb}(\lambda_2) \end{bmatrix} \cdot \begin{bmatrix} \Delta C_{HbO_2} \\ \Delta C_{Hb} \end{bmatrix} = \begin{bmatrix} \dfrac{\ln\dfrac{I_0(\lambda_1)}{\Delta I(\lambda_1)}}{d \cdot DPF(\lambda_1)} \\ \dfrac{\ln\dfrac{I_0(\lambda_2)}{\Delta I(\lambda_2)}}{d \cdot DPF(\lambda_2)} \end{bmatrix} \quad (6)$$

In Eq. (6), the molar extinction coefficients and $DPF(\lambda)$ can be obtained from the literature (Webster 2002; Duncan et al. 1995). Since change in the concentration of $HbO_2$ ($\Delta C_{HbO_2}$) and Hb ($\Delta C_{Hb}$) can be calculated, the change in oxygen saturation ($\Delta SO_2$) can be determined for the transient measurement. The complete derivation for Eq. (6) is provided in the Supplementary Methods section below.

Reflectance Oximeter Design and Placement

Figure 2A:
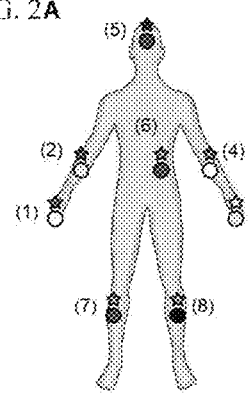
FIG. 2A shows pulsatile (ac) signal magnitude for red and NIR channels, where d=0.5 cm; sensor placement locations on the body are indexed from 1-8, while the fill color of the markers (* for red and ○ for NIR) shows the signal current at each location.
Figure 2B:
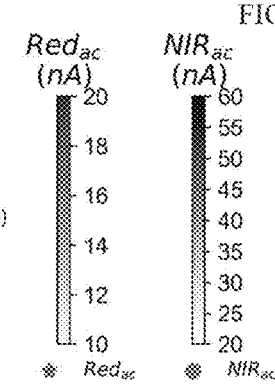
FIG. 2B shows stationary (dc) signal magnitude for red (Δ) and NIR ((▫)) channels.

Emitter-detector spacing (d) is an important design parameter for reflectance oximetry. To find the optimal spacing, d, a reflection-mode sensor board was utilized and the effect of d on PPG ac and dc signals was measured at the 8 locations of the body as depicted in FIG. 2A. The schematic of the sensor, containing three rings of four PDs spaced at 0.5, 0.8, and 1.1 cm away from the red and NIR LEDs at the center, is shown in FIG. 2C. Both ac and dc signal magnitude drops exponentially with increasing d. FIGS. 2D and 2E show ac and dc signals for d=0.5, 0.8, and 1.1 cm recorded on the wrist. When placed at d<0.5 cm, dc signal saturates the PD. This issue can be mitigated by putting an optical barrier between the LED and the PD to reduce direct coupling of light from the LED to the PD. While d=0.5 cm provided us the best SNR, d can be different for other sensor designs. The spacing is chosen so that there is a balance between a good ac signal magnitude and a reduced background noise. Optical flux output of the LEDs, external quantum efficiency (EQE) of the PD, and active area of the LEDs and the PD influence the optimum d for a reflection-mode sensor.

A similar approach is employed to find the optimal sensing location for $SpO_2^r$—the reflection-mode sensor was placed at 8 different location of the body as depicted in FIGS. 2A and B. FIG. 2A shows the pulsatile (ac) signal magnitude for red ($Red_{ac}$) and NIR ($NIR_{ac}$) channels with an emitter-detector spacing, d=0.5 cm. A high ac and a low dc signal are desirable for PPG measurements. The forehead provides the strongest ac signal—20 nA for red and 60 nA for NIR, making it the most suitable location for $SpO_2^r$. The signal strength drops roughly by half on the wrists. Although a clear degradation of the ac signal was observed on the ribcage and the legs, heart rate and oxygenation values could be extracted from the measured signal. Similar to the ac signal, the forehead provides the highest dc signal, while the ribcage demonstrates the lowest dc signal magnitude. FIG. 3 provides the full dataset of the ac and dc measurements at the 8 sensing locations for 5 subjects; the left panel shows the ac signal magnitudes, and the right panel shows the dc signal magnitudes for d=0.5, 0.8 and 1.1 cm.

As for wavelength dependence, the signal magnitude for NIR is higher than the visible spectrum because light attenuation in tissue for NIR is much less than the visible spectrum. Consequently, the optical flux requirement for oximetry is less stringent for NIR than visible colors—the NIR OLEDs used in the example ROA provide 0.2 mW of flux, compared to the 0.9 mW of flux of the red OLEDs at the operating condition of 10 $mAcm^{-2}$ (FIG. 4). With 0.7×0.7 cm active area for both OLEDs and OPDs, and 0.5 cm spacing between the OLEDs and OPDs, the dimension of the complete ROA is 4.3 cm in both length and width.

OLED and OPD Array Fabrication and Characterization

In an embodiment, an ROA is fabricated using four-pixel red and four-pixel NIR OLED arrays, along with an eight-pixel OPD array. The arrays are fabricated on separate substrates and then assembled together to form the ROA. FIG. 5 shows an ROA assembly according to an embodiment. Three layers of optoelectronics—(1) OPD array layer, (2) NIR OLED array layer, and (3) Red OLED array layer are fabricated on separate substrates in an embodiment. These layers may be fabricated on a single substrate in another embodiment, or on two substrates (e.g., two layers on one substrate and the third on another substrate). Any layers may then be stacked on one another: OPD array layer, NIR OLED array layer, and red OLED array layer, respectively, as shows, and connected to the control electronics via flat flex cable (FFC) connectors. The layers may be laser-cut so that one layer does not obstruct the other layer's optical path.

FIG. 6 shows a method flow for making an ROA including OLED and OPD arrays. The OLED and OPD array fabrication steps are shown side by side. For the OLED array, only one color of four pixels is shown for simplicity—the same fabrication steps are used for red and NIR OLEDs. For the OPD array, the complete array includes 8 pixels. OLED arrays are fabricated on top of PEN (Polyethylene Naphthalate) substrate(s) with patterned ITO (Indium Tin Oxide) for contacts in the embodiment shown. A surface energy patterning (SEP) step is then performed that creates hydrophilic regions where PEDOT:PSS (Poly(3,4-ethylenedioxythiophene)-Poly(Styrenesulfonate) is blade coated (FIG. 6, step A left panel). The interlayer and the emission layer are deposited using subsequent blade-coating steps (FIG. 6, step B left panel). Subsequently, the dielectric and the silver traces are printed using a screen printer (FIG. 6, step C left panel). The purpose of printing the dielectric is to prevent shorts between the underlying ITO strips to the silver traces. Finally, thermal evaporation is used to deposit calcium/aluminum to finish the fabrication of OLED arrays (FIG. 6, step D left panel). Each OLED pixel is encapsulated with UV curable epoxy and a plastic film in an embodiment. The OLED device stack is shown in FIG. 7A. The same process steps apply for both red and NIR OLEDs, only the active materials are different.

The OPD array is fabricated on a planarized PEN substrate in an embodiment. A PEDOT:PSS anode is blade coated using SEP technique as shown in FIG. 6, step A right panel. SEP processing for OPD is performed. A patterned anode is necessary because, without patterning, a large parasitic capacitance is formed between the PEDOT:PSS layer and the body, which may obscure the signal in noise. The active layer is then blade coated (FIG. 6, step B right panel). Next, silver traces are screen printed to connect the anodes and cathodes of each pixel to external circuitry as shown in FIG. 6, step C right panel. Finally, a cathode is formed, e.g., an aluminum cathode is evaporated, to complete the device stack, which is shown in FIG. 7B, according to an embodiment.

Steps E and F of FIG. 6 schematically show blade coating and screen printing techniques; the color bars on the left side of the fabrication steps A-C indicates the technique used for that respective layer—sky blue for blade coating (steps A and B) and red for screen printing (step C).

The OPD and OLED arrays are shown in FIG. 8A and FIG. 8B, respectively. The OPD array comprises 8 OPD pixels, where each OPD row contains 2 OPD pixels. Brown markers from darker to lighter shades are used to label row 1-4 of the OPD array. The same markers are used to present the performance characteristics of the OPD pixels. As for the 2×2 red and NIR OLED arrays, row 1 and 3 contains the four red OLED pixels, and row 2 and 4 contains the four NIR OLED pixels. The ROA is formed by stacking the OLED and OPD arrays. The arrays are assembled as such so that emitter-detector spacing, e.g. of 0.5 cm, is maintained.

The performance parameters of the OPD array are shown in FIGS. 8C-E. The shade of brown lines indicates the row position of the pixels in the array as shown in FIG. 8A. An average EQE of 30% is observed across the absorption spectrum (FIG. 8D) with dark currents of a few nA/cm$^2$ (FIG. 8C). The cutoff frequency is measured at over 5 kHz for OPDs as shown in FIG. 8E. Since the operation frequency of the pulse oximeters is generally less than 1 kHz, this bandwidth is sufficient for oximetry.

The OLEDs show turn-on voltages at around 3V as designated in the J-V characteristics in FIG. 8F. The OLEDs are operated at 10 mAcm$^{-2}$ for oximetry, where the red OLEDs provide 0.9 mW of flux, while the NIR OLEDs provide 0.2 mW of flux. The EQE values at operating conditions—~8-10% for red OLEDs and ~2-3% for NIR OLEDs. The OLEDs demonstrate a change in performance parameter depending on the row position due to the decrease in active layer thickness in the blade coating direction, this variability can be mitigated by continuously feeding ink in front of the blade coater. The variability in the OLED and OPD performance can be accommodated by taking a calibration measurement before using the array for oximetry. The emission spectrum of the OLEDs is shown in FIG. 8H, where the red OLED has a peak emission at 612 nm and the NIR OLED has a peak emission at 725 nm. FIG. 8G shows EQE as a function of current density of OLED arrays.

System Setup and Single Pixel Reflection-Mode Pulse Oximetry

The array implementation requires addressing individual pixels of the oximeter. Therefore, in certain embodiments, the hardware and software for the ROA are designed to support one or both of single pixel and array measurements. The system setup according to an embodiment is shown in FIG. 9A. The printed ROA is interfaced with the control electronics using FFC (Flexible Flat Cable) connectors. Each pixel of the ROA is composed of one red and one NIR OLED, and two OPDs. Signals from the red and NIR channels are read out sequentially using the two OPDs, and the average of the OPDs are used for signal processing. Using this format, the 4×4 device (OLEDs and OPDs) array provides 3×3 readout pixels. The pixels are selected using analog switches. A Texas Instruments Analog Front End (AFE) sequentially drives the OLEDs and reads out the OPD signal. The AFE is controlled by an Arduino Due microcontroller. Software control of the AFE allows flexibility in choosing OLED driving parameters, and also gives access to the variable OPD gain circuitry. Finally, the data is collected using an electronic interface such as a Universal Asynchronous Receiver/Transmitter (UART) interface, and processed using software. A photograph of a control electronics embodiment is shown in FIGS. 10A, 10B and 10C, and the photographs of a software Graphical User Interface (GUI) embodiment is shown in FIGS. 11A and 11B.

To test the reflectance oximeter in the single-pixel mode, a setup was used where oxygenation of a volunteer can be varied by varying the oxygen concentration of the air the volunteer breathes in as depicted in FIG. 9B. An altitude simulator is used to change the oxygen concentration of the air the volunteer breathes in via a facemask. A high altitude setting in the altitude simulator reduces the oxygen concentration and a low altitude setting in the altitude simulator increases the oxygen concentration of the air. Depending on the oxygen concentration of the air, the volunteer's oxygenation changes. This change in oxygenation is then picked up by a commercial finger probe sensor and using the reflection-mode sensor on the forehead. Calculated oxygen saturation using the commercial probe ($SpO_2^t$) and the reflectance probe ($SpO_2^r$) are shown in FIG. 9C and FIG. 9D. The oxygen concentration ($O_2$%) was varied from 21% to 15% over a period of 8 minutes (FIG. 9C and FIG. 9D blue dotted lines in upper graphs). During the first 30 s, a baseline oxygen concentration of 21% was set, then reduced to 17.5% at t=30 s; after keeping $O_2$% at 17.5% for 120 s, $O_2$% was further reduced to 15% at t=150 s and was kept at that level for 150 s. Then $O_2$% was brought back to the baseline of 21%.

Calculated oxygen saturation using the pulse oximetry model as described in Eq. (3) for transmission and reflection-mode are shown in the FIG. 9C and FIG. 9D, in the bottom graphs with purple lines. For the transmission-mode probe, oxygen saturation ($SpO_2^t$) changes from 96% to 90.5%, then comes back up to 94.5%. For the reflection-mode probe on the forehead oxygen saturation ($SpO_2^r$) changes from 98% to 90.4%, then comes back up to 93.5%. A 1.1% mean error between $SpO_2^t$ and $SpO_2^r$ was observed over the period of 8 minutes. The PPG signals for both transmission and reflection-mode probes are shown in FIG. 9E and FIG. 9F. Red and NIR channel data are shown for 240 s<t<245 s. PPG signal peaks and calculated heart rate from the PPG peaks show almost identical results for both $SpO_2^t$ and $SpO_2^r$. Here, an error of 0.85% is seen between $SpO_2^t$ and $SpO_2^r$, which falls within the 1-2% error margin that is inherent to pulse oximetry.

In-Vivo 2D Oxygen Saturation Monitoring

The pulse oximetry model is applicable when there is a pulsatile arterial blood signal. In the case of low blood perfusion, medical shock, or organ injury, the pulsatile arterial blood signal becomes too weak. For the aforementioned scenarios, or places on the body that have a low pulsatile signal, a modified oximetry measurement model as described in Eq. (6) can be used. For monitoring local changes in tissue oxygenation, blood flow to a volunteer's arm was controlled. By restricting blood supply to the arm with a pressure cuff, temporary ischemia to the arm was induced by inflating the pressure cuff to 50 mmHg over the systolic pressure. An ROA was used to monitor the change in oxygen saturation ($\Delta SO_2$) under normal condition and under pressure cuff-induced ischemia with the ROA. The measurement setup is shown in FIG. 12A, where the ROA is used to measure $\Delta SO_2$ on the forearm, while the pressure cuff is utilized to control blood supply to the arm, subsequently changing $\Delta SO_2$ of the sensed tissue. FIGS. 13A, 13B and 13C show that before and after inducing ischemia, there is a pulsatile arterial blood signal, which can be used with the pulse oximetry model as described in Eq. (3), when the blood supply is restricted only reflectance oximetry can be performed to measure $\Delta SO_2$, which is described in Eq. (6).

Similar to the single pixel measurement, the ROA was used to measure $\Delta SO_2$ under normal condition and under ischemia. The ROA included 4×4 OLED and OPD devices, which provides 3×3 oximeter pixels. These pixels are indexed pixel 1-9, (Px1-Px9) are shown in FIG. 12B. A raster scan from Px1 to Px9 is used to collect data from the tissue. After collecting data from all 9 pixels, 2D contour maps of red and NIR channels and $\Delta SO2$ are created. For the in-vivo 2D oxygen saturation monitoring test, data during the first 30 s are collected under normal condition and is considered the baseline. The pressure cuff is then used to induce ischemia, therefore the signal amplitude in the red and NIR signal channels gradually decreases. Once the pressure is released the signals overshoot, going over the baseline (FIG. 12C). FIG. 12D show the 2D maps of red and NIR signal channels, and $\Delta SO_2$ during the test under normal condition (t=0 s), under ischemia (t=60,120 s), and after releasing the pressure cuff (t=180,240 s). Since this is a transient measurement, $\Delta SO_2$ remains at the baseline ($\Delta SO_2=0\%$) at t=0 s, under ischemia $\Delta SO_2$ drops to −9.3% at t=150 s, after releasing the pressure-cuff $\Delta SO_2$ increases to +8.4% at t=180 s. The 2D contours maps may be created at every 30 s interval or other interval as desired. The results obtained in this test agree with the studies reported in the literature on pressure cuff-induced ischemia.

Example Methods

Fabrication and Characterization of the OLED Arrays

The OLED arrays were printed on ITO pattered PEN substrates. Two 1 cm wide ITO strips were placed 1.1 cm apart from each other, for creating the two columns of the OLEDs. The substrate was placed on a hotplate at 80° C. for 3 hrs under vacuum. The sample was then taken out in the air and placed on a hotplate at 180° C. for 1 hr. Then the substrate was treated with heptadecaflouropolymer in order to make the surface hydrophobic. The treated substrate was kept in a nitrogen-filled chamber overnight. OLEDs were blade coated using the semiconducting polymers (provided by Cambridge Display Technologies Ltd.) to form the emissive layer of the OLEDs. After all the layers were blade coated, the samples were transferred to a thermal evaporator in a glovebox to evaporate calcium and aluminum to finish the OLED stack. Before screen printing, the OLEDs were taken out of the glovebox for measurement, they were encapsulated by face sealing using a UV curable epoxy (Delo Katiobond LP612) and plastic film (PQA1) on top. A power source unit (Keithley 2600) was used to sweep voltage across the devices and an integrating sphere (Orb Optronix SP-75 spectrometer) was used to measure flux out of the OLEDs.

Fabrication and Characterization of the OPD Array

The OPD array was printed on top of planarized PEN substrates (TeiJin PQA1) using blade coating techniques. The substrate was first plasma treated in Tegal Plasmod at 50 W for 10 s. The substrate was then placed in a vacuum with 40 μL of heptadecaflouropolymer for 20 mins to render substrate hydrophobic. A stainless steel stencil with cutouts of the desired PEDOT:PSS area was placed on top of the substrate, then treated for 1.2 mins of oxygen plasma in a Diener Nano plasma system. 30 μL of PEDOT:PSS was dispensed uniformly in front of the blade. Then ink was blade-coated with a blade height of 100 μm and speed of 1 cms$^{-1}$. The substrate was then annealed for 10 mins at 120° C. The substrate was then plasma treated in Tegal Plasmod at 50 W for 10 s. 50 μL of 1:2 CDT Donor:PC71BM in 95:5 3,3',5,5'-Tetramethylbenzidine:Benzyl Benzoate (TMB:BB) was dispensed at the top of the array. Then ink was blade-coated with a blade height of 200 μm and speed of 2.5 cms$^{-1}$. The substrate was then annealed for 1.5 hrs at 120° C. Next, silver flake paste was screen-printed on top of the array and then annealed in a glove box for 5 mins at 120° C. Finally, aluminum cathode at a base pressure of $5 \cdot 10^{-6}$ Torr at a rate of 3-5 Ås$^{-1}$ was evaporated to finish the OPD stack.

Control Electronics for the ROA

The control electronics were designed to support reflectance oximetry in the single pixel and the array mode. Additionally, the system was designed to measure oxygenation with or without the pulsatile arterial blood signal. We used a Texas Instruments Analog Front End (AFE4490) to sequentially drive the OLEDs and read out the OPD signal. OLED arrays and the OPD array were interfaced with the control electronics using FFC connectors. The pixels in the array were selected using analog switches (Analog Devices ADG1608). The AFE was controlled with an Arduino Due microcontroller. Software control of the AFE allowed flexibility in choosing OLED driving parameters and allowed adjustments to the variable OPD gain circuitry. Finally, the data was collected using a Universal Asynchronous Receiver/Transmitter (UART) interface and processed using software.

Reflection-Mode Pulse Oximetry ($SpO_2^r$) Data Collection and Processing

For monitoring oxygenation in the presence of a pulsatile signal, the oxygenation of the volunteer was changed by using an altitude simulator (Everest Summit II—Altitude Generator). Altitude of 5000 and 8000 ft corresponds to an oxygen concentration of 17.5% and 15% respectively. The change in oxygen concentration changed oxygen saturation of the volunteer, which was monitored using a transmission mode oximeter probe on the finger ($SpO_2^t$), and the printed reflectance probe on the forehead ($SpO_2^r$). Data for the red and NIR channels were collected for both $SpO_2^t$ and $SpO_2^r$ simultaneously using the control electronics. PPG peaks, heart rate, and the ratio of the ratios of the red and NIR PPG signals were calculated, then a modified Beer-Lambert's law (Eq. (3)) in addition to an empirical correction was used to calculate both $SpO_2^t$ and $SpO_2^r$.

Reflectance Oximetry Data Collection and Processing

For measuring oxygenation in the absence of a pulsatile arterial blood signal, forearm ischemia was induced in human volunteers using a pressure cuff. After taking a baseline measurement, the pressure-cuff was used to induce ischemia using a pressure of 50 mmHg over the systolic pressure. The cuff was released after 2 mins of ischemia. Data was recorded for 5 mins to observe the change in oxygenation using the ROA. A raster scan from Pixel1 (Px1) to Pixel9 (Px9) was used to collect data from the tissue. A modified model as described in Eq. (6) was used to monitor oxygenation of tissue. Data from the 9 pixels were plotted using nearest-neighbor interpolation to create the 2D spatial maps of red and NIR channels, and the change in oxygenation.

The flexible reflectance oximeter array (ROA) embodiments disclosed herein may be used beyond the conventional sensing locations because of the novel sensor configurations. The mechanical flexibility, 2D oxygenation mapping capability, and the ability to place the sensor in various locations make the ROA embodiments promising for novel medical sensing applications such as mapping oxygenation in tissues, wounds, skin grafts, or transplanted organs.

Supplemental Methods

Reflection-Mode Pulse Oximetry ($SpO_2^r$)

Oxygen saturation in reflection-mode pulse oximetry ($SpO_2^r$) can be expressed as the ratio of the concentrations of oxygenated arterial blood over the sum of the concentrations of oxygenated ($C_{HbO_2}$) and deoxygenated ($C_{Hb}$) arterial blood:

$$SpO_2^r = \frac{C_{HbO_2}}{C_{HbO_2} + C_{Hb}} \quad (7)$$

If light emitters and detectors are placed on the same side of the tissue, a modified Beer-Lambert's law can be used to model the light propagation as shown in FIG. 1B and the equation below:

$$I(\lambda) = I_0(\lambda) e^{-\mu_a(\lambda) \cdot d \cdot DPF(\lambda)} \quad (8)$$

where, $I(\lambda)$ is the measured diffused reflected light intensity, $I_0(\lambda)$ is the incident light intensity, $\mu_a(\lambda)$ is the absorption coefficient of the sensed tissue, d is the distance between the light emitter and detector, i.e., the emitter-detector spacing, and $DPF(\lambda)$ is the differential pathlength factor (DPF), which accounts for the multiple scattering of light in tissue.

The absorbance, A, can be defined as:

$$A(\lambda) = -\ln \frac{I(\lambda)}{I_0(\lambda)} = \mu_a(\lambda) \cdot d \cdot DPF(\lambda) \quad (9)$$

Now if one considers attenuation in skin, tissue, and bones—represented with the subscript dc, and attenuation in oxygenated and deoxygenated blood—represented with the subscripts Hb $O_2$ and Hb, the following equations represent measured light intensities at diastole and systole of the cardiac cycle:

$$I_{high,dia}(\lambda) = \quad (10)$$
$$I_0(\lambda) e^{-\mu_{a,dc}(\lambda) \cdot d_{dc} \cdot DPF(\lambda)} \cdot e^{-(\varepsilon_{HbO_2}(\lambda) C_{HbO_2} + \varepsilon_{Hb}(\lambda) C_{Hb}) d_{dia} \cdot DPF(\lambda)}$$

$$I_{low,sys}(\lambda) = \quad (11)$$
$$I_0(\lambda) e^{-\mu_{a,dc}(\lambda) \cdot d_{dc} \cdot DPF(\lambda)} \cdot e^{-(\varepsilon_{HbO_2}(\lambda) C_{HbO_2} + \varepsilon_{Hb}(\lambda) C_{Hb}) d_{sys} \cdot DPF(\lambda)}$$

Light has to pass through an additional optical path $\Delta d$ at systole, therefore $d_{sys} = d_{dia} + \Delta d$. Additionally, a normalization step ($I_{normalized} = I/I_{high,dia}$) is required to determine the normalized systolic intensity. Now Eq. 11 can be rewritten, $$I_{norm}(\lambda) = \frac{I(\lambda)}{I_{high,dia}(\lambda)} \quad (12)$$

$$I_{norm,sys}(\lambda) = e^{-(\varepsilon_{HbO_2}(\lambda) C_{HbO_2} + \varepsilon_{Hb}(\lambda) C_{Hb}) \Delta d \cdot DPF(\lambda)} \quad (13)$$

$R_{os}$ is the ratio of absorbances in two different wavelengths, $$R_{os} = \frac{A_{\lambda_1}}{A_{\lambda_2}} = \frac{\ln I_{norm,sys,\lambda_1}}{\ln I_{norm,sys,\lambda_2}} \quad (14)$$

Now, rearranging Eq. 7, $$C_{HbO_2} = SpO_2^r (C_{HbO_2} + C_{Hb}) \quad (15)$$

$$C_{Hb} = (1 - SpO_2^r)(C_{HbO_2} + C_{Hb}) \quad (16)$$

After the normalizing step described in Eq. 12, absorbance, A, can be written as, $$A(\lambda) = (\varepsilon_{HbO_2}(\lambda) C_{HbO_2} + \varepsilon_{Hb}(\lambda) C_{Hb}) \cdot \Delta d \cdot DPF(\lambda) \quad (17)$$

Inserting concentrations of oxygenated and deoxygenated blood, $$A(\lambda) = \quad (18)$$
$$(\varepsilon_{HbO_2}(\lambda) SpO_r^2(C_{HbO_2} + C_{Hb}) + \varepsilon_{Hb}(\lambda)(1 - SpO_r^2)(C_{HbO_2} + C_{Hb})) \cdot \Delta d \cdot DPF(\lambda)$$

$$= (\varepsilon_{HbO_2}(\lambda) SpO_r^2 + \varepsilon_{Hb}(\lambda)(1 - SpO_r^2))(C_{HbO_2} + C_{Hb}) \cdot \Delta d \cdot DPF(\lambda) \quad (19)$$

The ratio of the absorbances at the two different wavelengths can be found using the following equation, $$R_{os} = \frac{A_{\lambda_1}}{A_{\lambda_2}} = \frac{(\varepsilon_{\lambda_1,HbO_2} SpO_r^2 + \varepsilon_{\lambda_1,Hb}(1 - SpO_2^r))}{(\varepsilon_{\lambda_2,HbO_2} SpO_r^2 + \varepsilon_{\lambda_2,Hb}(1 - SpO_2^r))} \cdot \frac{(C_{HbO_2} + C_{Hb}) \cdot \Delta d \cdot DPF_{\lambda_1}}{(C_{HbO_2} + C_{Hb}) \cdot \Delta d \cdot DPF_{\lambda_2}} \quad (20)$$

$$= \frac{A_{\lambda_1}}{A_{\lambda_2}} = \frac{(\varepsilon_{\lambda_1,HbO_2} SpO_r^2 + \varepsilon_{\lambda_1,Hb}(1 - SpO_2^r)) \cdot DPF_{\lambda_1}}{(\varepsilon_{\lambda_2,HbO_2} SpO_r^2 + \varepsilon_{\lambda_2,Hb}(1 - SpO_2^r)) \cdot DPF_{\lambda_2}} \quad (21)$$

Finally, oxygen saturation, $SpO_2^r$ can be calculated using Eq. (22). Where, ($\varepsilon_{\lambda,HbO_2}$) and ($\varepsilon_{\lambda,Hb}$) are the molar extinction coefficient of oxyhemoglobin and deoxyhemoglobin at each wavelength.

$$R_{os} = \frac{AC_{\lambda_1}/DC_{\lambda_1}}{AC_{\lambda_2}/DC_{\lambda_2}},$$

ratio of ac to dc signal at each channel, is conventionally used for $S_pO_2^t$. Similar approach is taken for $S_pO_2^r$ with $$R'_{os} = \frac{R_{os}}{\frac{DPF_{\lambda_1}}{DPF_{\lambda_2}}},$$

where DPF accounts for the multiple scattering in the reflection mode.

$$SpO_2^r(R'_{os}) = \frac{\varepsilon_{\lambda_1,Hb} - \varepsilon_{\lambda_2,Hb} R_{os}'}{(\varepsilon_{\lambda_1,Hb} - \varepsilon_{\lambda_1,HbO_2}) + (\varepsilon_{\lambda_2,HbO_2} - \varepsilon_{\lambda_2,Hb}) R_{os}'} \quad (22)$$

Similar to the transmission-mode pulse oximetry, $R_{os}'$ can be obtained from a calibration curve to provide $SpO_2^r$.

Reflectance Oximetry

PPG signal from pulsatile arterial blood is essential for pulse oximetry. Therefore, in the case of low perfusion or in the absence of pulsatile arterial blood signal, pulse oximetry in both transmission and reflection mode cannot be performed. In these scenarios, Eq. (8) can be rewritten to measure the time-varying light intensity attenuation, $\Delta I(\lambda)$ in blood and tissue, where $\Delta\mu_a$ expresses the change in absorption during the measurement.

$$\Delta I(\lambda) = I_0(\lambda) e^{-\mu_a(\lambda) \cdot d \cdot DPF(\lambda)} \quad (23)$$

Now, $\Delta\mu_a(\lambda)$ can be expressed as the sum of the specific absorption coefficients $\varepsilon_{HbO_2}(\lambda)$, $\varepsilon_{Hb}(\lambda)$, of HbO2 and Hb, times the concentration, $C_{HbO_2}$ and $C_{HbO_2}$:

$$\Delta\mu_a(\lambda) = \varepsilon_{HbO_2}(\lambda) \cdot \Delta C_{HbO_2} + \varepsilon_{Hb}(\lambda) \cdot \Delta C_{Hb} \quad (24)$$

Rewriting Eq. (23), $$\varepsilon_{HbO_2}(\lambda) \cdot \Delta C_{HbO_2} + \varepsilon_{Hb}(\lambda) \cdot \Delta C_{Hb} = \frac{\ln\frac{I_0(\lambda)}{\Delta I(\lambda)}}{d \cdot DPF(\lambda)} \quad (25)$$

Since there are two wavelength channels, a system of linear equations can be established:

$$\varepsilon_{HbO_2}(\lambda_1) \cdot \Delta C_{HbO_2} + \varepsilon_{Hb}(\lambda_1) \cdot \Delta C_{Hb} = \frac{\ln\frac{I_0(\lambda_1)}{\Delta I(\lambda_1)}}{d \cdot DPF(\lambda_1)} \quad (26)$$

$$\varepsilon_{HbO_2}(\lambda_2) \cdot \Delta C_{HbO_2} + \varepsilon_{Hb}(\lambda_2) \cdot \Delta C_{Hb} = \frac{\ln\frac{I_0(\lambda_2)}{\Delta I(\lambda_2)}}{d \cdot DPF(\lambda_2)}$$

$$\begin{bmatrix} \varepsilon_{HbO_2}(\lambda_1) & \varepsilon_{Hb}(\lambda_1) \\ \varepsilon_{HbO_2}(\lambda_2) & \varepsilon_{Hb}(\lambda_2) \end{bmatrix} \cdot \begin{bmatrix} \Delta C_{HbO_2} \\ \Delta C_{Hb} \end{bmatrix} = \begin{bmatrix} \frac{\ln\frac{I_0(\lambda_1)}{\Delta I(\lambda_1)}}{d \cdot DPF(\lambda_1)} \\ \frac{\ln\frac{I_0(\lambda_2)}{\Delta I(\lambda_2)}}{d \cdot DPF(\lambda_2)} \end{bmatrix}$$

In Eq. (26), the molar extinction coefficients and $DPF(\lambda)$ can be obtained from the literature. Since change in the concentration of $HbO_2$ ($\Delta C_{HbO_2}$) and Hb ($\Delta C_{Hb}$) can be calculated, the change in oxygen saturation ($\Delta SO_2$) can be determined for the transient measurement.

U.S. patent application Ser. No. 15/414,397, corresponding to U.S. patent Application Publication No. 2017/0156651 A1, which is incorporated herein by reference, discloses various aspects of PPG measurements, including reflectance-based measurements, as well as useful PPG device materials. All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Various embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this specification includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. An oximeter device, comprising:
a first array of first light emitting elements configured to emit only red light;
a second array of second light emitting elements, wherein each second light emitting element is configured to emit only green light or near-infrared (NIR) light, wherein the first array and the second array are arranged on at least one flexible substrate in an interleaved manner; and
an array of sensor elements arranged on the at least one flexible substrate, wherein each sensor element is configured to detect red and green light or red and NIR light, and to output a signal representing an amount of red or green or NIR light detected, wherein the first array and the second array and the array of sensor elements form a plurality of measurement pixels, wherein each measurement pixel consists of one of said first light emitting elements and a corresponding sensor element adjacent thereto, and one of said second light emitting elements and a different corresponding sensor element adjacent thereto.

2. The oximeter device of claim 1, wherein each of said first light emitting elements and each of said second light emitting elements comprises an organic light emitting diode (OLED), and wherein each of said sensor elements comprises an organic photodiode (OPD).

3. The oximeter device of claim 1, further including control electronics electronically coupled with the first light emitting elements, the second light emitting elements, and the sensor elements and configured to control activation of the first and second light emitting elements and receive the signals output by the sensor elements.

4. The oximeter device of claim 3, wherein the control electronics includes a signal processor configured to receive and process the signals output by the sensor elements to produce signals that represent blood oxygenation content.

5. The oximeter device of claim 1, wherein the at least one flexible substrate comprises polyethylene naphthalate (PEN).

6. The oximeter device of claim 1, wherein each of said sensor elements is configured to detect the emitted red or green or NIR light reflected by tissue containing blood.

7. The oximeter device of claim 1, wherein the first array and the second array are arranged on a first flexible substrate in the interleaved manner, wherein the array of sensor elements are arranged on a second flexible substrate, and wherein the first flexible substrate and the second flexible substrate are coupled together to form the plurality of interleaved measurement pixels.

8. The oximeter device of claim 1, wherein the first array is arranged on a first flexible substrate and the second array is arranged on a second flexible substrate, wherein the array of sensor elements are arranged on a third flexible substrate, and wherein the first flexible substrate, the second flexible substrate and the third flexible substrate are coupled together to form the plurality of interleaved measurement pixels.

9. A flexible oximeter device, comprising:
a first N×M array of first light emitting elements configured to emit only red light;
a second N×M array of second light emitting elements, wherein each second light emitting element is configured to emit only green light or near-infrared (NIR); and
a third array of 2*N*M sensing elements, each sensing element being configured to detect red and green light or red and NIR light and to output a signal representing an amount of red or green or NIR light detected, wherein N and M are each equal to or greater than 1;
wherein the first array, the second array and the third array are arranged on at least one flexible substrate in an interleaved manner forming a (2N−1)×(2M−1) array of interleaved measurement pixels, wherein each said measurement pixel comprising consists of one of said first light emitting elements and a corresponding sensing element, and one of said second light emitting elements and a different corresponding sensing element.

10. The flexible oximeter device of claim 9, wherein N=M, and wherein N is greater than or equal to 2.

11. The flexible oximeter device of claim 9, wherein a first spacing between each sensing element and each first light emitting element and a second spacing between each sensing element and each second light emitting element are the same.

12. The flexible oximeter device of claim 11, wherein the first and second spacings are each between 0.5 cm and 1.0 cm.

13. The flexible oximeter device of claim 9, wherein each of said first light emitting elements and each of said second light emitting elements comprises an organic light emitting diode (OLED), and wherein each of said sensing elements comprises an organic photodiode (OPD).

14. The flexible oximeter device of claim 9, wherein the at least one flexible substrate comprises polyethylene naphthalate (PEN).

15. The flexible oximeter device of claim 9, wherein the first N×M array and the second N×M array are arranged on a first flexible substrate, and wherein the third array of sensing elements is arranged on a second flexible substrate that is attached to the first flexible substrate.

16. The flexible oximeter device of claim 9, wherein each said sensing element is configured to detect emitted red or green or NIR light reflected by tissue containing blood.

17. A method of spatially mapping oxygenation content in a tissue sample, the method comprising:
placing an oximeter device having an array of interleaved measurement pixels proximal to an area of a tissue sample, each said measurement pixel corresponding to a different measurement location of the area of the tissue sample, wherein each measurement pixel consists of one first light emitting element configured to emit only red light and a first corresponding sensing element adjacent thereto, and one second light emitting element configured to emit only green light or only NIR light and a second corresponding sensing element adjacent thereto;
taking measurements of the tissue sample using each measurement pixel in an order; and
creating a map of oxygenation content of the area of the tissue sample based on the measurements taken of the tissue sample.

18. The method of claim 17, wherein each of the first corresponding sensing element and the second corresponding sensing element is configured to detect red and green light or red and NIR light.

19. The method of claim 18, wherein each of said first light emitting elements and each of said second light emitting elements comprises an organic light emitting diode (OLED), and wherein each of said sensing elements comprises an organic photodiode (OPD).

20. The method of claim 17, wherein taking measurements includes, for each said measurement pixel, activating the first light emitting element, detecting a reflected red light signal using the first corresponding sensing element, activating the second light emitting element, and detecting a reflected green or NIR light signal using the second corresponding sensing element.

21. The method of claim 17, wherein the order of taking measurements is a sequential order.

22. The method of claim 17, wherein the area of the tissue sample exhibits a pulsatile arterial blood signal.

23. The method of claim 17, wherein the area of the tissue sample does not exhibit a pulsatile arterial blood signal.

24. The method of claim 17, further including displaying a representation of the map of oxygenation content of the area of the tissue sample on a display device.

* * * * *